(12) United States Patent
Grossman et al.

(10) Patent No.: US 7,232,807 B2
(45) Date of Patent: Jun. 19, 2007

(54) COMPOSITIONS AND METHODS FOR BINDING AGGLOMERATION PROTEINS

(75) Inventors: Abraham Grossman, Pleasantville, NY (US); Valentine M. Kryukov, Puschino (RU); Brian Neil Zeiler, Washington Township, NJ (US)

(73) Assignee: Oligomerix, Inc., New York, NY (US)

( * ) Notice: Subject to any disclaimer, the term of this patent is extended or adjusted under 35 U.S.C. 154(b) by 0 days.

(21) Appl. No.: 11/112,953

(22) Filed: Apr. 22, 2005

(65) Prior Publication Data

US 2006/0024697 A1 Feb. 2, 2006

Related U.S. Application Data

(63) Continuation of application No. 10/343,694, filed as application No. PCT/US02/16922 on May 30, 2002.

(60) Provisional application No. 60/294,822, filed on May 31, 2001.

(51) Int. Cl.
  *C07H 21/02* (2006.01)
  *C07H 21/00* (2006.01)
  *A61K 31/70* (2006.01)
  *C12N 15/11* (2006.01)

(52) U.S. Cl. .................. 514/44; 536/25.6; 536/23.1; 977/704

(58) Field of Classification Search .................. None
See application file for complete search history.

(56) References Cited

U.S. PATENT DOCUMENTS 5,876,930 A 3/1999 Livak et al. ............ 435/6

(Continued)

FOREIGN PATENT DOCUMENTS

WO 8809810 12/1988

(Continued)

OTHER PUBLICATIONS

Weiss et al., RNA Aptamers Specifically Interact With the Prion Protein PrP; J. Of Virology, Nov. 1997, vol. 71, No. 11, pp. 8790-8797.

(Continued)

*Primary Examiner*—Bruce R. Campell
*Assistant Examiner*—Benjamin P. Blumel
(74) *Attorney, Agent, or Firm*—Davidson, Davidson & Kappel, LLC

(57) ABSTRACT

Amplibody compositions and methods used to interact with agglomeration proteins are disclosed herein. Compositions herein comprise one or more DNA or RNA molecules having affinity for at least one agglomeration protein. The nucleic acid component is a naturally or non-naturally occuring molecule with twenty or more ribonucleotide bases. For RNA, at least one nucleotide sequence portion of this RNA molecule has affinity to at least one consensus sequence present in the agglomeration RNA-binding protein. The portion of nucleotide sequence of RNA having affinity for agglomeration proteins is a sequence that is derived from either and RNA virus, and RNA agglomeration proteins is a sequence that is derived from either and RNA virus, an RNA phage, a messenger RNA ("mRNA"), a ribosomal RNA ("rRNA"), a transfer RNA ("tRNA"), a sequence that is received as a template by one or more RNA dependent RNA polymerases, or a combination thereof. Methods disclosed herein are directed towards detecting the presence of one or more agglomeration proteins in a sample matrix using the amplibody compositions described herein.

1 Claim, 20 Drawing Sheets

SEQ. ID NO. 6

U.S. PATENT DOCUMENTS

| | | | |
|---|---|---|---|
| 5,932,711 A | 8/1999 | Boles et al. | 536/23.1 |
| 6,225,058 B1 * | 5/2001 | Munishkin et al. | 435/6 |
| 6,426,409 B1 | 7/2002 | Winnacker et al. | 536/23.1 |
| 6,916,613 B2 * | 7/2005 | Munishkin et al. | 435/6 |
| 2002/0197737 A1 | 12/2002 | Mandelkow et al. | 436/518 |
| 2004/0005543 A1 | 1/2004 | Grossman et al. | |
| 2005/0261486 A1 | 11/2005 | Grossman et al. | |
| 2005/0266401 A1 | 12/2005 | Grossman et al. | |
| 2005/0266402 A1 | 12/2005 | Grossman et al. | |

FOREIGN PATENT DOCUMENTS

| | | |
|---|---|---|
| WO | 8910134 | 11/1989 |
| WO | 9715685 | 5/1997 |

OTHER PUBLICATIONS

Holeman et al., Isolation and Characterization of Fluorophore-Binding RNA Aptamers, Folding and Design; Oct. 30, 1998, vol. 3, No. 6, pp. 423-431.

Shi et al., RNA Aptamers as Effective Protein Antagonists in a Multicellular organism; Proceedings of the National Academy of Science USA, Aug. 1999, vol. 96, No. 18, pp. 10033-10038.

Scheffer et al., Interaction of 68-kDa TAR RNA-Binding Protein and other Cellular Proteins with Prion Protein_RNA Stem Loop; Neurovirol, 1995 vol. 1, pp. 391-398.

Battle and Doudna, "The Stem-loop Binding Protein Forms a Highly Stable and Specific Complex with the 3' Stem-loop of Histone Mrna," 2001 RNA 7:123-32.

Carp et al., "Scrapie Strain-specific Interactions with Endogenous Murine Leukamia Virus," 1999 J Gen Virol 80(Pt 1):5-10.

Cordeiro et. al., "Dna Converts Cellular Prion Protein into the β-sheet Conformation and Inhibits Prion Peptide Aggregation," 2001 J Biol Chem 276(52):49400-9.

Endo and Wool, "The Site of Action of A-sarcin on Eucariotic Ribosomes," 1982, J. Biol. Chem. 257(15):9054-60.

Gabus et al., "The Prion Protein Has RNA Binding and Chaperoning Properties Characteristic of Nucleocapsid Protein Nc P7 of HIV-1," 2001b J Biol Chem 276(22):19301-9.

Jiang et al., "Anchoring and Extended HTLV-1 Rex peptide within an RNA Major Groove Containing Junctional Base Triples," 1999 Structure Fold Des. 7(12):1461-72.

Letsinger et al., "Cholesteryl-conjugated Oligonucleotides: Synthesis, Properties, and Activity as Inhibitors of Replication of Human Immunodeficiency Virus in Cell Culture," (1989) Proc. Natl. Acad. Sci. USA 86:6553-6556.

Lemaitre et al., "Specific Antiviral Activity of a Poly(L-Lysine)-conjugated Oligodeoxyribonucleotide Sequence Complimentary to Vesticular Somatitis Virus N Protein mRNA initiation site," (1987) Proc. Natl. Acad. Sci. USA 84:648-652.

Lochrie et. al., "In vitro selection of RNAs that bind to the human immunodeficiency virus type-1 gag polyprotein," 1997 NAR 25(14):2902-10.

Meyer et. al., "A Monomer-Dimer Equilibrium of a Cellular Prion Protein (PrP$^c$) Not Observed with Recombinant PrP," 2000, J Biol Chem Dec. 1, 275(48):38081-7.

Murdoch, et al., "Potential Retroviral RNA's in Creutzfeldt-Jakob Disease," 1990 Virology 64(4):1477-86.

Munishkin et. al., "Efficient Templates for Qβ Replicase are Formed by Recombination from Heterologous Sequences," 1991, J Mol Bio 221(2):463-72.

Narang, "A Critical Review of the Nature of the Spongiform Encephalopathy Agent: Protein Theory Versus Virus Theory," 1998 Res Virol 149(6):375-82.

Pan et al., "Conversion of α-helices into β-sheets features in the formation of the scrapie prion proteins," 1993 PNAS, USA 90:10962-66.

Zeiler et. al, "Improved Approach to RNA and Protein Recognition for Pathogen Detection," 2000, Proceedings of SPIE Aerosense 2000, 4036:103-14.

Gabus et al., "The Prion Protein Has RNA Binding and Chaperoning Properties Characteristic of Nucleocapsid Protein NCp7 of HIV-1," The Journal of Biological Chemistry, vol. 276, No. 22, pp. 19301-19309, Jun. 1, 2001.

Goeddel; "Systems for Heterologous Gene Expression," Gene Expression Technology: Methods in Enzymology 185, Academic Press, San Diego, Calif., pp. 3-7, (1990).

Gottesman, S., "Minimizing Proteolysis in *Escherichia coli*: Genetic Solutions," Gene Expression Technology: Methods in Enzymology 185, Academic Press, San Diego, Calif.; pp. 119-128 (1990).

Akowitz et al., "Endogenous Viral Complexes with Long RNA Cosediment with the Agent of Creutzfeldt-Jakob Disease," Nucleic Acids Research, 1994, vol. 22, No. 6, pp. 1101-1107.

Amann et al., "Tightly Regulated *tac* Promoter Vectors Useful for the Expression of Unfused and Fused Proteins in *Escherichia Coli*," Gene 69 (1988), pp. 301-315.

Hegde et al., "A Transmembrane Form of the Prion Protein in Neurogenerative Disease," 1998 Science 279(5352):827-34.

Hermann and Westhof, "Non-Watson-Crick base pairs in RNA-protein Recognition," 1999 Chem Biol 6(12)-R335-43.

Hermann and Patel, "Adaptive Recognition by Nucleic Acid Aptamers," 2000 Science 287(5454):820-5.

Iwai et al., "Recognition of the High Affinity Binding Site in Rev-response Element RNA by the Human Immunodeficiency Virus Type-1 rev Proten," 1992, Nucleic Acid Research 20(24):6465-72.

Chesebro et al., "Identification of Scrapie Prion Protein-Specific mRNA in Scrapie-Infected and Uninfected Brain," Nature vol. 315, pp. 331-333, May 23, 1985.

Current Protocols in Molecular Biology, John Wiley & Sons, NY (1989); Sections 6.3.1-6.3.6.

Nandi, Polymerization of Human Prion Peptide HuPrP 106-126 to Amyloid In Nucleic Acid Solution, 1998 Arch Virol 143(7):1251-63.

Nandi and Leclerc, "Polymerization of Murine Recombinant Prion Protein in Nucleic Acid Solution," 1999 Arch Virol 144(9):1751-63.

Nandi and Sizaret,"Murine Recombinant Prion Protein Induces Ordered Aggregation of Linear Nucleic Acids to Condensed Globular Structures," 2001 Arch Virol 146:32745.

Narang, "Evidence That Single-stranded DNA Wrapped Around the Tubulofilamentous Particles Termed "Nemaviruses" is the Genome of the Scrapie Agent," Res. Virol. 1998, 149, pp. 375-382.

Oesch et al., "A Cellular Gene Encodes Scrapie PrP 27-30 Protein," 1985 Cell 40:735-46.

Patel, "Adaptive Recognition in RNA Complexes with Peptides and Protein Modules," 1999 Curr Opin Struct Biol 9(1):74-87.

Preuβ et al., "Probing RNA-Protein Interactions Using Pyrene-Labeled Oligodeoxynucleotides: Qβ Replicase Efficiently Binds Small RNAs by Recognizing Pyrimidine Residues," 1997 J. Mol. Biol., Oct. 31, 273(3):600-13.

Puglisi and Williamson, "RNA Interaction with Small Ligands and Peptides," 1999 in the RNA World, R F Gesteland, T R Cech, J F Atkins, eds., Cold Spring Harbor Laboratory Press, Cold Spring Harbor, N.Y., 2d, 1999, pp. 403-425.

Rochet and Lansbury Jr., "Amyloid Fibrillogenesis:Themes and Variations," 2000 Curr Opin Struct Biol 10:60-8.

Smith, D. B. and Johnson, K. S., "Single-step Purification of Polypeptides Expressed in *Escherichia coli* as Fusions with Glutathione S-transferase," (1988) Gene 67:31-40.

Studier et al., "Use of T7 RNA Polymerase to Direct Expression of Cloned Genes," Gene Expression Technology: Methods In Enzymology 185, Academic Press, San Diego, Calif. (1990) 60-89.

Tanchou et al., "Formation of Stable and Functional HIV-1 Nucleoprotein Complexes in Vitro," 1995 J Mol Biol 252:563-71.

Wada et al., "Codon Usage Tabulated From the GenBank Genetic Sequence Data," (1992) Nucleic Acids Res. 20:2111-2118.

Weissmann, "A 'Unified Theory' of Prion Propagation," 1991 Nature 352:679-83.

Yehiely et al., "Identification of Candidate Proteins Binding to Prion Protein," 1997, Neurobiology of Disease 3:339-355.

Ye et al., "Deep Penetration of an a -helix Into a Widened RNA Major Groove in the HIV-1 Rev Peptide-RNA Aptamer Complex," Dec. 1999 Nat Struct Biol. 3(12):1026-33.

Ye et al., "RNA Architecture Dictates the Conformations of a Bound Peptide," 1999 Chem Biol 6(9):657-69.

\* cited by examiner

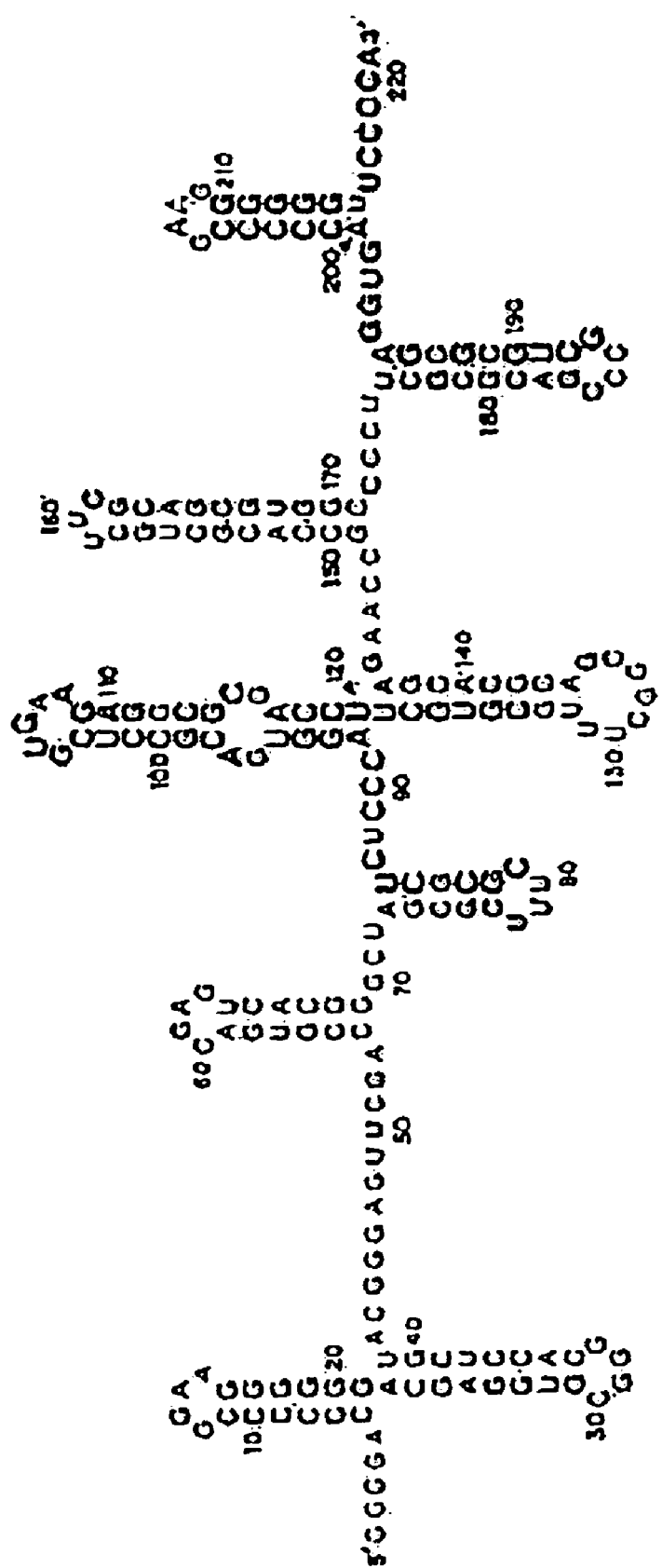
FIG. 1 (a)   SEQ. ID NO. 1

SEQ. ID NO. 1

SEQ. ID NO. 2

SEQ. ID NO. 3

SEQ. ID NO. 4

SEQ. ID NO. 6

SEQUENCE LISTING

<160> NUMBER OF SEQ ID NOS: 10

<210> SEQ ID NO 1
<211> LENGTH: 221
<212> TYPE: DNA
<213> ORGANISM: Artificial
<220> FEATURE:
<223> OTHER INFORMATION: ARTIFICAL SEQUENCE VARIANT FROM A VIRUS
<220> FEATURE:
<221> NAME/KEY: variation
<222> LOCATION: (1)..(221)

<400> SEQUENCE: 1

```
ggggacccccc cggaaggggg gacgaggtgc gggcacctcg tacgggagtt cgaccgtgac    60
gagtcacggg ctagcgcttt cgcgctctcc caggtgacgc ctcgtgaaga ggcgcgacct   120
tcgtgcgttt cggcgacgca cgagaaccgc cacgctgctt cgcagcgtgg cccctttcgcg   180 cagcccgctg cgcgaggtga cccccgaagg ggggttcccc a                       221
```

<210> SEQ ID NO 2
<211> LENGTH: 86
<212> TYPE: DNA
<213> ORGANISM: Artificial
<220> FEATURE:
<223> OTHER INFORMATION: ARTIFICAL SEQUENCE VARIANT FROM A VIRUS

<400> SEQUENCE: 2

```
gggttcatag cctattcggc ttttaaagga ccttttttccc tcgcgtagct agctacgcga    60
ggtgaccccc cgaaggggggg tgcccc                                         86
```

<210> SEQ ID NO 3
<211> LENGTH: 130
<212> TYPE: DNA
<213> ORGANISM: Artificial
<220> FEATURE:
<223> OTHER INFORMATION: ARTIFICAL SEQUENCE VARIANT FROM A VIRUS

<400> SEQUENCE: 3

```
gggttcatag cctattcggc ttcgcgcatg ggaatttgag ggacgatggg gaagtgggag    60
cgcgttttaa aggaccttttt tccctcgcgt agctagctac gcgaggtgac ccccgaagg   120 ggggtgcccc                                                          130
```

<210> SEQ ID NO 4
<211> LENGTH: 118
<212> TYPE: DNA
<213> ORGANISM: Artificial
<220> FEATURE:
<223> OTHER INFORMATION: ARTIFICAL SEQUENCE VARIANT FROM A VIRUS

<400> SEQUENCE: 4

```
gggttcatag cctattcggc ttcgcgcccg tttataatac ttagtgagcg cgttttaaag    60 gaccttttttc cctcgcgtag ctagctacgc gaggtgaccc cccgaagggg ggtgcccc    118
```

<210> SEQ ID NO 5
<211> LENGTH: 118
<212> TYPE: DNA
<213> ORGANISM: Artificial
<220> FEATURE:
<223> OTHER INFORMATION: ARTIFICAL SEQUENCE VARIANT FROM A VIRUS

<400> SEQUENCE: 5

```
gggttcatag cctattcggc ttcgcgcccc tggggtttgc ctcaggagcg cgttttaaag      60
gacctttttc ccttgcgtag ctagctacgc gaggtgaccc cccgaagggg ggtgcccc       118
```

<210> SEQ ID NO 6
<211> LENGTH: 196
<212> TYPE: RNA
<213> ORGANISM: Artificial
<220> FEATURE:
<223> OTHER INFORMATION: ARTIFICAL SEQUENCE VARIANT FROM A VIRUS

<400> SEQUENCE: 6

```
gggguuucca accggaauuu gagggaugcc uaggcauccc ccgugcgucc cuuuacgagg      60
gauugucgac ucuagucgac gucugggcga aaaauguacg agaggaccuu uucgguacag    120
acgguaccug agggaugccu aggcaucccc cgcgccgguu ucggaccucc agugcguguu    180
accgcacugu cgaccc                                                    196
```

<210> SEQ ID NO 7
<211> LENGTH: 26
<212> TYPE: RNA
<213> ORGANISM: Artificial
<220> FEATURE:
<223> OTHER INFORMATION: ARTIFICAL SEQUENCE VARIANT FROM A VIRUS

<400> SEQUENCE: 7

```
gggaauuuga ggacgauggu aagugg                                          26
```

<210> SEQ ID NO 8
<211> LENGTH: 29
<212> TYPE: RNA
<213> ORGANISM: Artificial
<220> FEATURE:
<223> OTHER INFORMATION: ARTIFICAL SEQUENCE VARIANT FROM A VIRUS

<400> SEQUENCE: 8

```
gggaauuuga ggaacgauag guaagugga                                       29
```

<210> SEQ ID NO 9
<211> LENGTH: 55
<212> TYPE: RNA
<213> ORGANISM: Artificial
<220> FEATURE:
<223> OTHER INFORMATION: ARTIFICAL SEQUENCE VARIANT FROM A VIRUS

<400> SEQUENCE: 9

```
ggccccguaa cuucgggaga aggggugcuc uguuagggug caagcccgag agagc          55
```

<210> SEQ ID NO 10
<211> LENGTH: 157
<212> TYPE: RNA
<213> ORGANISM: Artificial
<220> FEATURE:
<223> OTHER INFORMATION: ARTIFICAL SEQUENCE VARIANT FROM A VIRUS

<400> SEQUENCE: 10

```
gggguuucga accggaauuu gagggaugcc uaggcauccc ccgugcgucc cuuuacgagg      60
gauugucgac ucuagaggau ccgguaccug agggaugccu aggcaucccc gcgccggu      120 uucggaccuc cagugcgugu uaccgcacug ucgaccc                             157
```

COMPOSITIONS AND METHODS FOR BINDING AGGLOMERATION PROTEINS

RELATED APPLICATION

This application is a continuation of U.S. application Ser. No. 10/343,694, filed on Jun. 26, 2003, which is a 371 of PCT/US02/16922, filed on May 30, 2002, which claims benefit of 60/294,822, filed on May 31, 2001, the disclosures of which are hereby incorporated by reference.

FIELD OF THE INVENTION

The present invention pertains to compositions and methods used to interact with proteins. In particular, this invention is directed toward compositions and methods used to interact with proteins putatively involved in protein agglomeration or plaque formation within tissue.

BACKGROUND OF THE INVENTION

Essentially there are two types of nucleic acid found in living cells. One is deoxyribonucleic acid ("DNA"), and the other is ribonucleic acid (RNA"). Under normal physiological conditions, both of these nucleic acid molecules are associated with proteins. These proteins can include scaffolding proteins, enzymes, ligases, telomerases, etc. These nucleic acid binding proteins perform functions necessary for normal metabolism and cell/tissue viability.

A significant portion of RNA-binding proteins ("RNP") mediate post-transcriptional regulation of gene expression. Heterogenous nuclear RNAs ("hnRNA") are the primary transcripts of protein encoding genes. These transcripts (hnRNA) are processed in the nuclei of eukaryotic cells and, at least a portion of such hnRNAs, become messenger RNAs ("mRNAs"). From the time hnRNAs emerge from the transcriptional complex, and throughout the time they are in the nucleus, they are associated with proteins termed hnRNA proteins. Members of this family of proteins are required for multiple steps during mRNA metabolism, including pre-mRNA processing and mRNA localization, translation and stability. The majority of proteins associated with RNAs appear to be associated with hnRNAs and mRNAs in hnRNP and mRNA complexes.

However, some disease processes appear to involve the formation of RNA-mediated protein agglomerations. These agglomerations have been shown to be associated with neuronal cell death and brain wasting disease. Spongiform encephalopathies, often involved with certain neuronal cell death and brain wasting syndromes, characteristically have protein plaques or agglomerations made manifest upon dissection. In spongiform encephalopathies, prions are thought to be the etiologic agent. Prion-based diseases result from "infectious proteins" that are involved in protein agglomeration.

It is believed that these protein agglomeration diseases are associated with certain RNA molecules. For example, viral RNPs and their concomitant RNA and protein components define much of the disease processes involved in viral pathogenicity (e.g., HIV, Dengue virus, etc.). With this in mind, bacterial and viral RNP complexes are considered to be attractive diagnostic targets.

A need currently exists for compositions and methods that can be used in the detection of proteins involved in the pathogenic agglomeration process.

SUMMARY OF THE INVENTION

The present invention pertains to compositions and methods used to interact with proteins. In particular, this invention is directed toward compositions and methods used to interact with proteins putatively involved in protein agglomeration or plaque formation within tissue, especially brain tissue.

Compositions of the present invention comprise one or more nucleic acid molecules, for example ribonucleic acid ("RNA") or deoxyribonucleic acid ("DNA") having affinity for at least one agglomeration protein The RNA or DNA component is a naturally or non-naturally occurring molecule with twenty or more nucleotide bases. (The term "non-naturally occurring" is meant to indicate that the composition is being used in a purity or process context that is not to be found in nature.) At least one nucleotide sequence portion of this nucleic acid molecule has affinity to at least one consensus sequence present in the agglomeration nucleic acid-binding protein. In one embodiment, the portion of RNA having affinity for agglomeration proteins is a sequence that is derived from either an RNA virus, an RNA phage, a messenger RNA ("mRNA"), a ribosomal RNA ("rRNA"), a transfer RNA ("tRNA"), a sequence that is received as a template by one or more RNA dependent RNA polymerases, or a combination thereof.

A consensus sequence of the present invention refers to an RNA-binding motif present in a protein that recognizes single-stranded RNA secondary structural elements such as hairpin loops, bulge loops, internal loops, or single-stranded regions. Most RNA-binding proteins ("RNP") have a modular structure with one or more RNA-binding domains ("RBD") and another domain that mediates interaction with other proteins. The hallmark of RNP motifs are consensus sequences positioned about thirty amino acids apart in a RBD, composed of from about a hundred to several hundreds of amino acids. Most of the amino acids that participate in RNA binding are located in β-pleated sheets. These structural elements of RBD appear to provide an exposed platform to which RNA binds. The RNA, when bound, remains exposed (as opposed to buried in a fold or pocket) and accessible to other cellular factors. Many RNPs contain multiple RBDs and can therefore simultaneously bind to more than one RNA molecule.

As used herein, the term "affinity" means exhibiting an attraction or capacity for binding. A specific affinity is an attraction that is directed to a particular feature or sequence of a molecule.

Methods of the present invention are directed towards detecting the presence of one or more agglomeration proteins within a sample matrix. An affinity complex is formed by contacting the sample matrix with one or more probes. The probes of the present embodiment are the nucleic acid compositions of the instant invention.

Probes of the present method comprise one or more nucleic acid molecules having affinity for at least one agglomeration protein The RNA or DNA component is a naturally or non-naturally occurring molecule with twenty or more nucleotide bases. At least one nucleotide sequence portion of this nucleic acid molecule has affinity to at least one consensus sequence present in the agglomeration nucleic acid-binding protein. In one embodiment, the portion of RNA having affinity for agglomeration proteins is a sequence that is derived from either an RNA virus, an RNA phage, a mRNA, a rRNA, a tRNA, a sequence that is received as a template by one or more RNA dependent RNA polymerases, or a combination thereof.

The present method includes the detection of any affinity complex formed. The detection of an affinity complex is indicative of the presence of one or more agglomeration proteins present in the original sample matrix.

A kit for determining the presence or absence of one or more agglomeration proteins within a sample matrix is also disclosed herein. The kit comprises one or more probes. These probes comprise a naturally or non-naturally occurring RNA and/or DNA with twenty or more nucleotides, wherein at least one sequence portion of the nucleotides has affinity for one or more agglomeration proteins. In one embodiment, the affinity sequence portion of the probe is derived from either an RNA virus, an RNA phage, a nucleotide sequence that is received as a template by one or more RNA dependent RNA polymerases, a mRNA, a rRNA, a tRNA, or a combination thereof. It is intended that the kit of the present invention be used in conjunction with the method of the present invention.

BRIEF DESCRIPTION OF THE DRAWINGS

FIG. 10 is a graph representing competition binding data between PrP-Amp and either AP1 or MNV (SEQ ID No. 2);

DETAILED DESCRIPTION

Figure 1B:
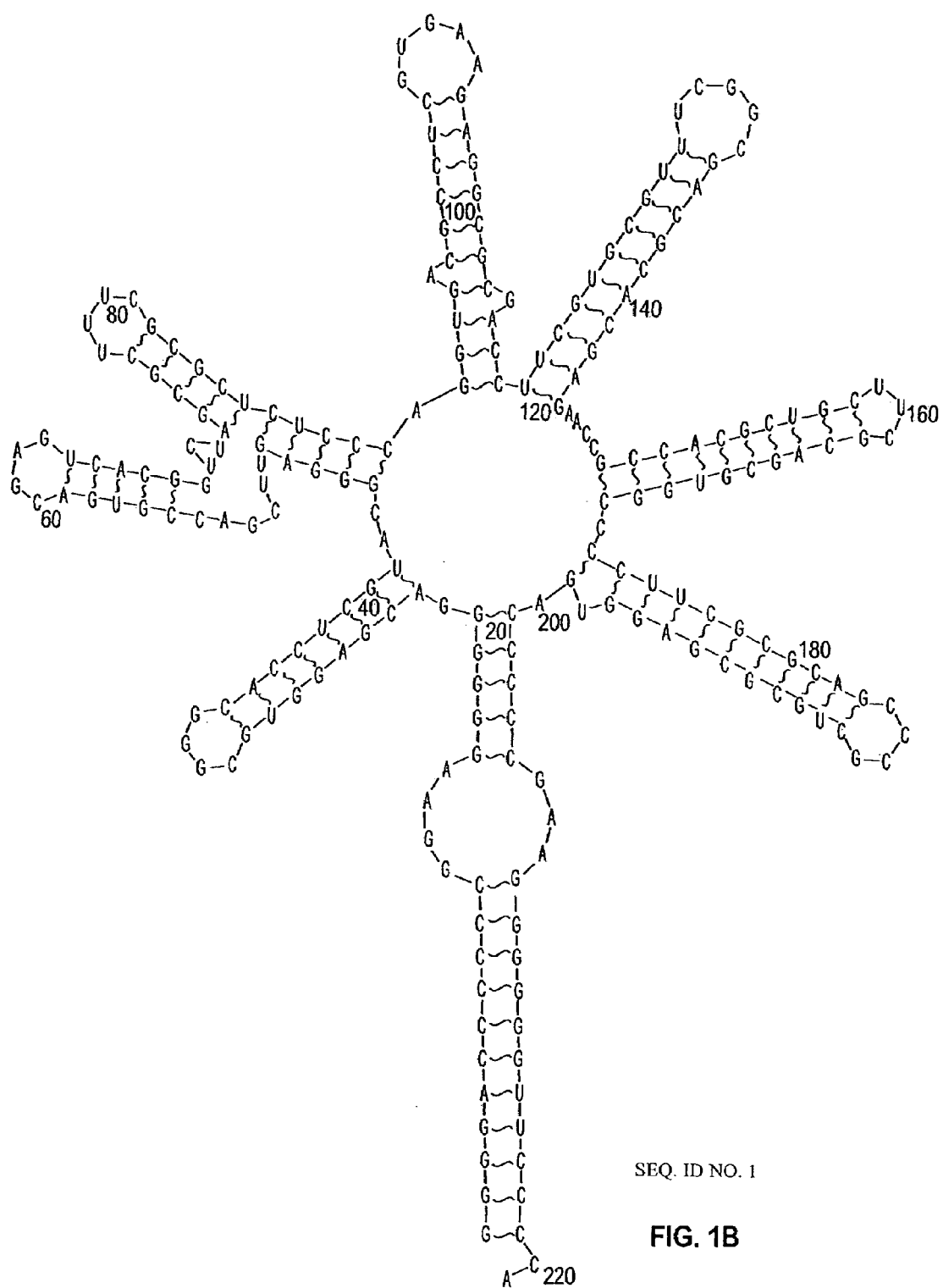
FIG. 1(a) depicts one embodiment of secondary structure for MDV RNA (SEQ ID No. 1), and (b) depicts a second embodiment of secondary structure for MDV RNA (SEQ ID No. 1)
Figure 2:
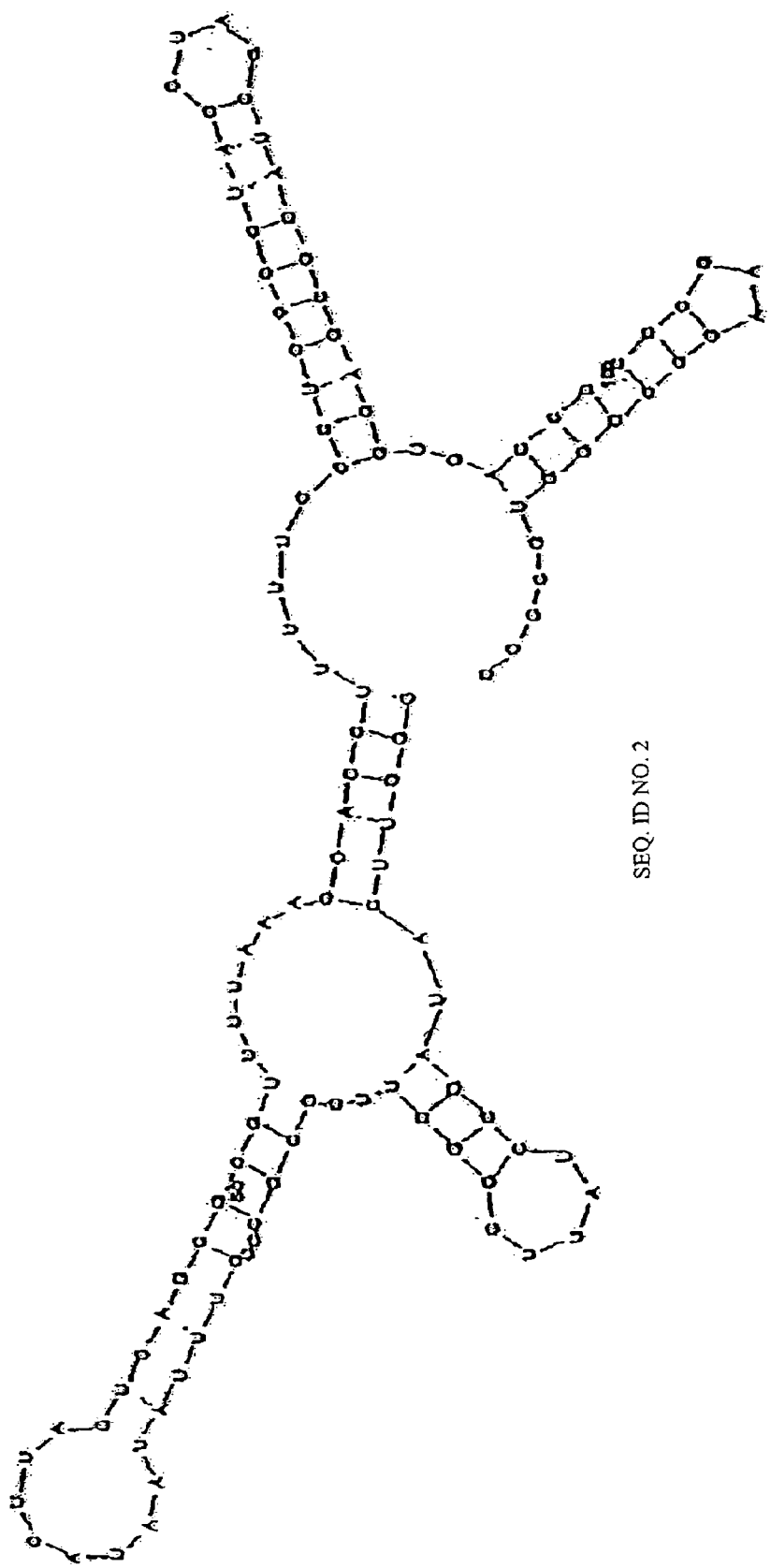
FIG. 2 depicts a secondary structure for MNV RNA (SEQ ID No. 2)
Figure 3:
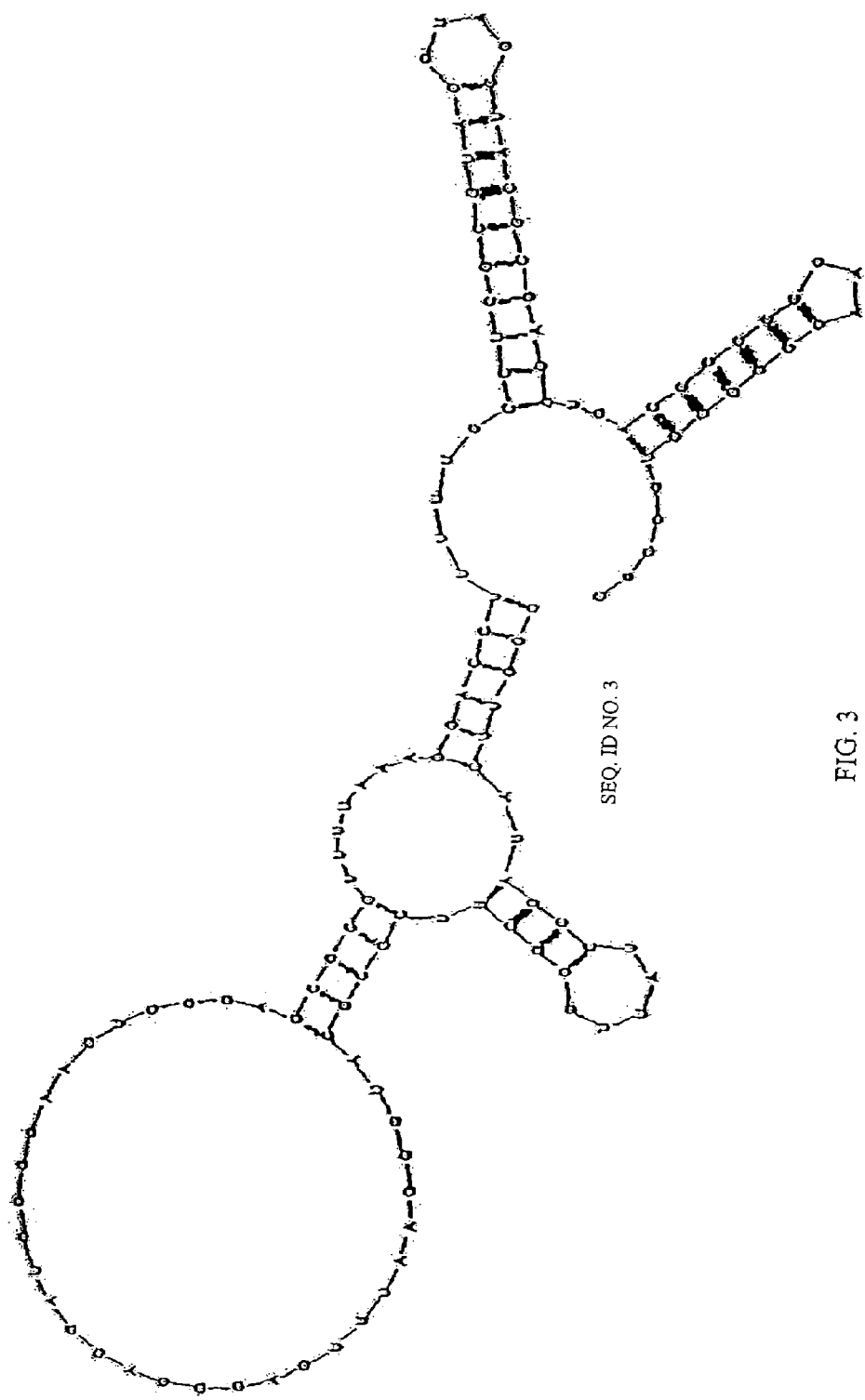
FIG. 3 depicts a secondary structure for MNV:AP1 RNA (SEQ ID No. 3)
Figure 4:
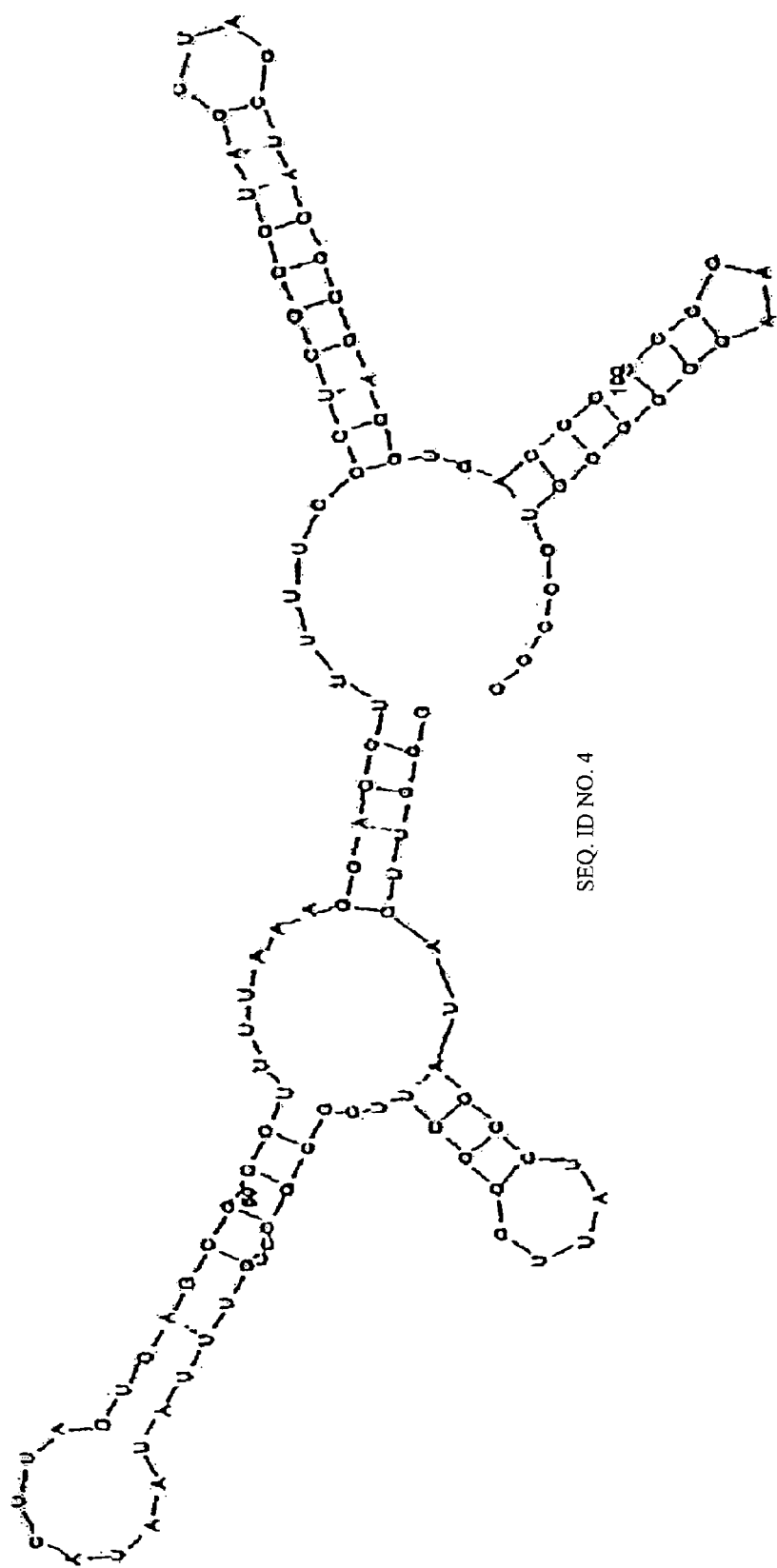
FIG. 4 depicts a secondary structure for MNV-1 RNA (SEQ ID No. 4)
Figure 5:
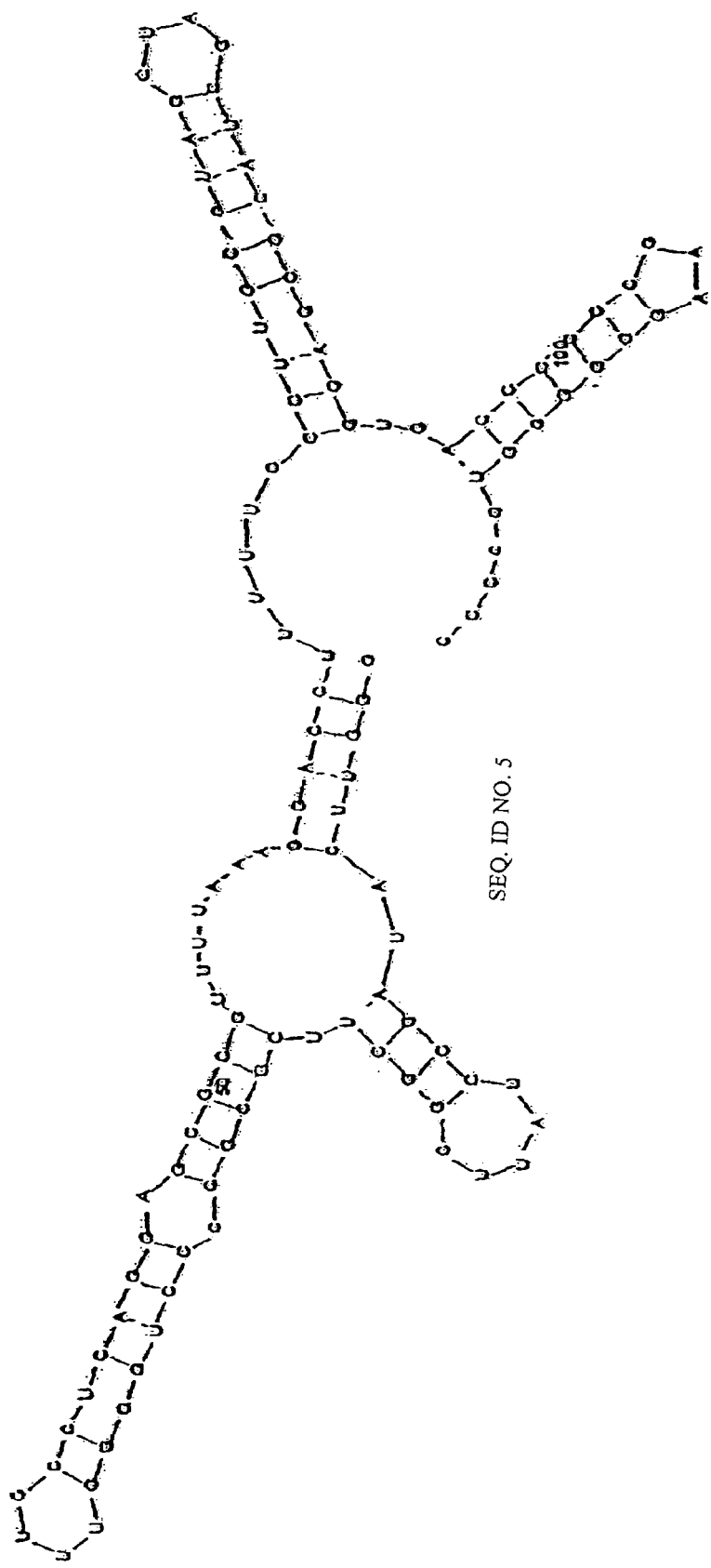
FIG. 5 depicts a secondary structure for MNV-2 RNA (SEQ ID No. 5)
Figure 6:
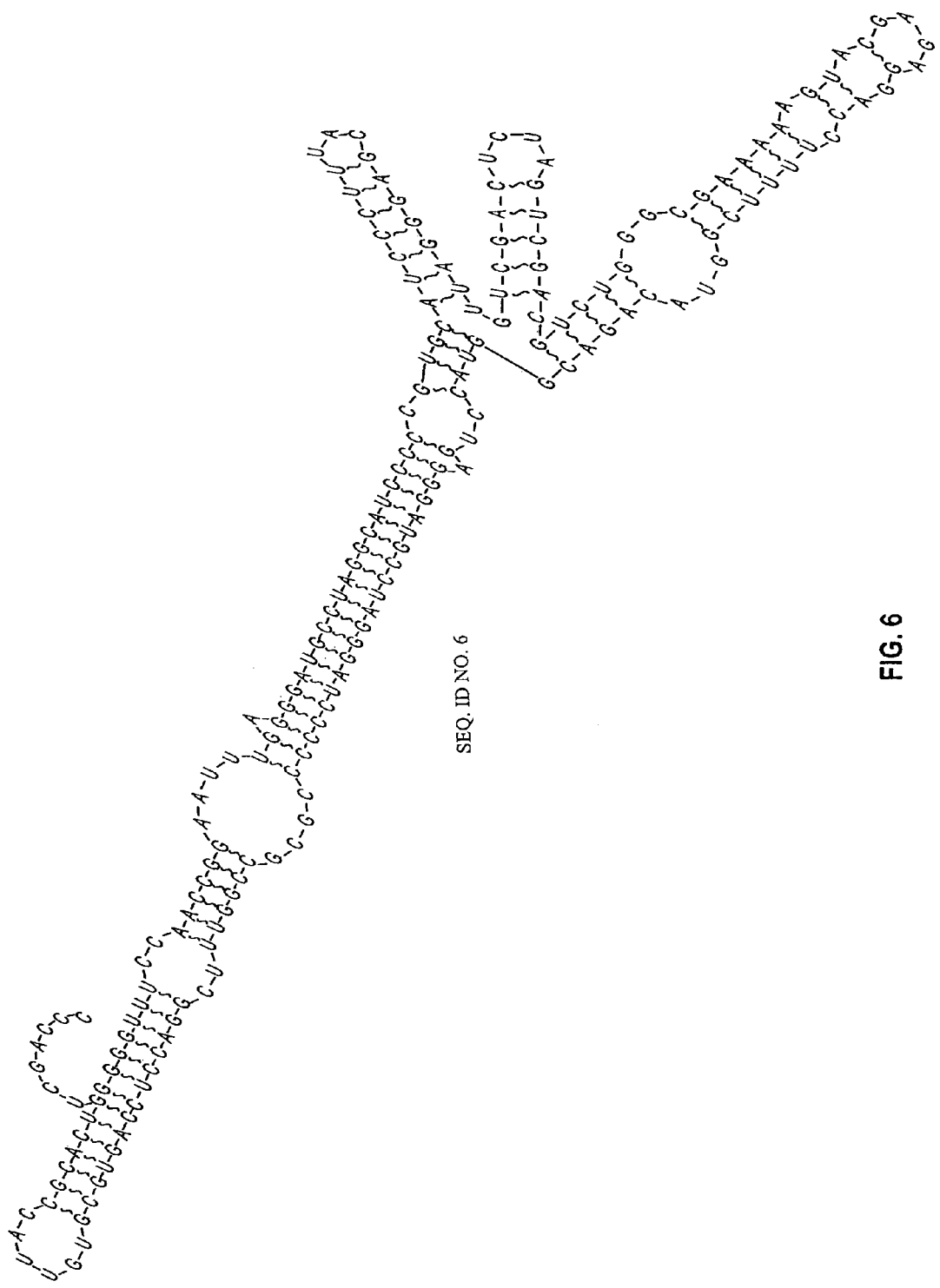
FIG. 6 depicts a secondary structure for RQ11+12 RNA (SEQ ID No. 6)

The present invention pertains to amplifiable nucleic acid antibodies that have affinity for agglomeration proteins. The invention also pertains to methods used to interact with such proteins using the compositions of the instant invention. Further, a kit for detecting the presence or absence of agglomeration proteins in a sample matrix is also disclosed.

Proteins bind to nucleic acids, either DNA or RNA. This binding is often facilitated by the secondary structure assumed by the nucleic acid. For example, loops and bulges of nucleotides are often involved in protein binding. Protein agglomeration can be facilitated by such nucleic acid binding. Isolation and characterization of nucleic acids having affinity for agglomeration proteins will aid in understanding and treatment of diseases involving protein agglomeration. This invention is directed toward this goal.

Proteins that bind to RNA (hereinafter referred to as "RNP") typically have RNA-binding motifs. Under suitable conditions, RNPs can non-specifically bind to nucleic acids having gross features that are recognized by the protein without regard to particular nucleotides or nucleotide sequences. It is generally believed that a nucleic acid's higher ordered structure is what provides binding recognition to the protein. For example, RNA is notorious for possessing secondary structures like loops that may in turn serve as structural motifs used for binding with RNPs. This notion is amenable to analysis simply by taking a primary nucleotide sequence of an RNA molecule that binds to a particular protein and changing the nucleotide sequence of a particular secondary structure, like a loop, in order to knock-out the structure and determining the binding avidity between the mutated RNA and protein.

Stringent in vitro assays have demonstrated that heterogeneous nuclear RNA-binding proteins (hnRNP) have different preferences for specific RNA sequences. One study examined the binding of various hnRNAs to various RNAs under 2M NaCl conditions resulting in a finding of striking avidity of hnRNPs for their preferred RNAs. These studies indicate that different hnRNP, and apparently other RNPs, discriminate among and between different RNAs. This property of discrimination can be exploited in the isolation, purification and classification of various groups of RNPs.

The molecular architecture of RNPs was studied in detailed using hnRNPs. However, the general principles gained through studying the hnRNP systems are applicable to other RNPs. Most RNPs have a modular structure with one or more RNA-binding domains (RBD) and special domains that mediate interaction with another protein. The hallmarks of RBDs in RNPs are distinct consensus sequences separated from each other by stretches of approximately thirty amino acids. Most of the amino acids that are involved in binding RNA are located in β-pleated sheets. These particular structural elements of RBDs appear to provide an exposed surface that can serve as a platform to which an RNA molecule can bind. The RNA, when bound, remains exposed (as opposed to being buried within a pocket of the protein) and thus accessible to other proteins. Many RNPs contain more than one RBD and can therefore bind to multiple RNA sequences or interact with multiple RNA molecules simultaneously.

Interaction between RNA and RNP is considered to be similar to the interaction between an antibody and its respective cognate antigen, in respect to their mutual affinity and specificity. The present invention is based upon this analogous system. The RNA compositions of the present invention perform like antibodies whose affinity is for one or more agglomeration proteins. These antibody-like RNA compositions are referred to herein as "amplibodies." Amplibodies are essentially nucleic acid antibodies. The term "amplibody" extends to DNA molecules that perform the same function. These amplibodies are amplifiable by techniques well developed in molecular biology. These nucleic acid antibodies, or amplibodies, can be directed at any number of targets. For example, amplibodies can be directed toward prion proteins involved in neurological diseases such as spongiform enchephalitis. Amplibodies can comprise artificial, synthetic nucleotide sequences that a skilled practitioner can insert by methods well known in the art. Therefore, amplibodies can be chimeric engineered RNA sequences.

As mentioned above, amplibodies can be amplified using an RNA-dependent RNA polymerase. In one embodiment of the present invention, the polymerase is Q-Amp. Q-Amp is derived from Q-beta replicase. Q-beta replicase can be isolated and purified from Q-beta bacteriophage. The bacteriophage contains a plus-strand RNA. This plus-strand serves both as mRNA for viral protein synthesis and as a template for the RNA-depednent RNA polymerase, Q-beta replicase. In the presence of the plus-strand, and other cofactors, the enzyme Q-beta replicase synthesizes the complementary minus-strand RNA. The minus-strand, in turn, serves as a template for plus-strand synthesis. Q-Amp is derived from the Q-beta replicase and comprises eukaryotic elongation factor Ts (Ef-Ts), eukaryotic elongation factor Tu (Ef-Tu), S1 nuclease, and a Replicase component. (Q-Amp is available from Q-RNA, Inc, New York, N.Y.) Q-Amp recognizes specific RNA templates and can amplify them exponentially, for example up to one billion-fold, in fifteen minutes under isothermal conditions. Templates for Q-Amp can contain sequence insertions that may have specific functional applications, for example, sequences that increases the avidity between an amplibody and an agglomeration protein. It should be appreciated by those skilled in the art, that replicases other than Q-Amp and Q-beta replicase may be used and are considered to be within the scope of this invention.

Amplibody compositions of the present invention comprise one or more RNA or DNA molecules having affinity for at least one agglomeration protein. The nucleic acid component is a naturally or non-naturally occurring molecule with twenty or more nucleotide bases. In one embodiment, at least one nucleotide sequence portion of this RNA molecule has affinity to at least one consensus sequence present in the agglomeration RNA-binding protein. A "consensus sequence" of the present invention refers to an RNA-binding motif present in a protein that recognizes single-stranded RNA secondary structural elements such as hairpin loops, bulge loops, internal loops, or single-stranded regions. In one embodiment of the present invention, the portion of RNA polynucleotide having affinity for agglomeration proteins is a sequence that is derived from either an RNA virus, an RNA phage, a messenger RNA ("mRNA"), a ribosomal RNA ("rRNA"), a transfer RNA ("tRNA"), a sequence that is received as a template by one or more RNA dependent RNA polymerases, or a combination thereof.

The terms "virus" and "phage" will be used interchangeably throughout this disclosure to mean "virus and phage". In one aspect of the invention, the RNA virus is a retrovirus. The RNA virus can be selected from the group consisting of a human immunodeficiency virus (HIV), polio virus, influenza virus, smallpox virus, chicken pox virus, Herpes virus, varicella zoster virus, Epstein-Barr virus, cytomegalo virus, feline leukemia virus (FeLV), human T cell leukemia virus (HTLV), simian immunodeficiency virus (SIV), and combinations thereof.

The RNA template of the present invention is an RNA that can be received and amplified by Q-beta replicase, Q-Amp, and nucleic acid replicases for DNA or RNA. The skilled artisan will appreciate that any RNA dependent RNA polymerase ("RNA pol") that will amplify the amplibodies of the present invention are within the scope of this invention.

In one embodiment of the instant invention, the RNA template is selected from the group consisting of midi-varient RNA (MDV RNA (SEQ ID No. 1)), mini-varient RNA (MNV RNA (SEQ ID No. 2)), MNV-AP1 RNA (SEQ ID No. 3), MNVUP RNA (SEQ ID No. 4), MNVLO RNA (SEQ ID No. 5), RQ RNA, and combinations thereof.

The DNA sequence encoding MDV RNA (SEQ ID NO 1) is:

5' GGGGACCCCCCGGAAGGGGGGACGAGGTGCGGGCACCTCGTACGGGA
GTTCGACCGTGACGAGTCACGGGCTAGCGCTTTCGCGCTCTCCCAGGTGA
CGCCTCGTGAAGAGGCGCGACCTTCGTGCGTTTCGGCGACGCACGAGAAC
CGCCACGCTGCTTCGCAGCGTGGCCCCTTCGCGCAGCCCGCTGCGCGAGG
TGACCCCCGAAGGGGGGTTCCCCA 3'

The DNA sequence encoding MNV RNA (SEQ ID NO 2) is:

5' GGGTTCATAGCCTATTCGGCTTTTAAAGGACCTTTTTCCCTCGCGTA
GCTAGCTACGCGAGGTGAC CCCCCGAAGGGGGTGCCCC 3'

The DNA sequence encoding MNV-AP1 RNA (SEQ ID NO 3) is:

5' GGGTTCATAGCCTATTCGGCTTCGCGCATGGGAATTTGAGGGACGAT
GGGGAAGTGGGAGCGCGTTTTAAAGGACCTTTTTCCCTCGCGTAGCTAGC
TACGCGAGGTGACCCCCCGAAGGGGGGTGCCCC 3'

The DNA sequence encoding MNVUP RNA (SEQ ID NO 4) is:

5' GGGTTCATAGCCTATTCGGCTTCGCGCCCGTTTATAATACTTAGTGA
GCGCGTTTTAAAGGACCTTTTTCCCTCGCGTAGCTAGCTACGCGAGGTGA
CCCCCCGAAGGGGGGTGCCCC 3'

The DNA sequence encoding MNVLO RNA (SEQ ID NO 5) is:

5' GGGTTCATAGCCTATTCGGCTTCGCGCCCCTGGGGTTTGCCTCAGGA
GCGCGTTTTAAAGGACCTTTTTCCCTTGCGTAGCTAGCTACGCGAGGTGA
CCCCCCGAAGGGGGGTGCCCC 3'

The RNA sequence can be obtained using DNA that encodes for the RNA sequence. The DNA can be placed within a suitable vector followed by transfecting a suitable host with the vector using methods known to those skilled in the art. The transcripts can then be isolated by methods commonly known in the art.

In one aspect of this invention, these templates for the RNA pol (replicase) have at least one oligonucleotide sequence having affinity for an agglomeration protein. For example, MDV, (SEQ ID No. 1), MNV (SEQ ID No. 2), and RQ RNA templates can have incorporated into their respective sequences a series of guanine nucleotides. RQ11+12 (SEQ ID No. 6) is such a template.

5'GGGGUUUCCAACCGGAAUUUGAGGGAUGCCUAGGCAUCCCCCGUGCGU

CCCUUUACGAGGGAUUGUCGACUCUAGUCGACGUCUGGGCGAAAAAUGUA

CGAGAGGACCUUUUCGGUACAGACGGUACCUGAGGGAUGCCUAGGAUCCC

CCCGCGCCGGUUUCGOACCUCCAGUGCGUGUUACCGCACUG

UCGACCC 3'

The RNA of the present invention preferably has one or more loops or bulges characterized by non-Watson-Crick pairing. (See FIGS. 1-6). The non-Watson-Crick pairing refers to regions of an otherwise normal Watson-Crick base pairing, there is a region in which the nucleotides are not paired or the pair is not the conventional Watson-Crick base pairing. For example, the nucleotides are held in close proximity with a like nucleotide (e.g., purine-purine or pyrimidine-pyrimidine). A preferred bulge or loop has a grouping of guanine nucleotides in series, for example, in a quartet. This guanine feature often corresponds to a recognition sequence in an RNA pol. For example RQ11+12 (SEQ ID No. 6) comprises a sequence that is derived from the Rev protein binding site and a sarcin recognition site that presents a series of guanine nucleotides. See Iwai, S. et al., NAR 20(24): 6465-6472,1992; the teachings of which are incorporated herein by reference.

There is no absolute length requirement for participating polynucleotide sequences. However, a preferred range is from about 20 to about 10,000 nucleotides. One of ordinary skill in the art will be able to determine the appropriate length of nucleotide sequence to employ for the RNA amplibodies of the present invention. It should also be understood that the polynucleotide sequences of the instant invention can be embedded within longer strands of nucleic acids or associated with other molecules.

It is understood that complementary base-pairing of individual base pairs generally follows Chargaff's Rule wherein an adenine pairs with an uracil (or thymine if DNA) and guanine pairs with cytosine. However, there are modified bases that account for unconventional base-pairing. A modified nucleic acid is understood to mean herein a DNA or RNA nucleic acid molecule that contains chemically modified nucleotides. The term "nucleic acid analogue" is understood herein to denote non-nucleic acid molecules such as "PNA" and morpholino that can engage in base-pairing interactions with conventional nucleic acids. These modified bases and nucleic acid analogues are considered to be within the scope of the instant invention. For example, nucleotides containing deazaguaine and uracil bases can be used in place of guanine and thymine, respectively, to decrease the thermal stability of probes. Similarly, 5-methyl-cytosine can be substituted for cytosine in complexes if increased thermal stability is desired. Modification to the sugar moiety can also occur and is embraced by the present invention. For example, modification to the ribose sugar moiety through the addition of 2'-O-methyl groups which can be used to reduce the nuclease susceptibility of RNA molecules. Modifications occurring with different moieties of the nucleic acid backbone are also within the scope of this invention. For example, the use of methyl phosphate, methyl phosphonate or phosphorothioate linkages to remove negative charges from the phosphodiesters backbone can be used.

The inventors have conducted experiments showing multiple binding sites on the same agglomeration protein. These sites where shown to have affinity for different RNA polynucleotide compositions. The agglomeration protein studied was a prion protein (PrP), see Weiss, S. et al., J. Virol. 1997, November: 71(11): 8790-7; the entire teachings of which are incorporated herein by reference. Two RNA polynucleotides were examined, one is the MNV RNA (SEQ ID No. 2) and the other is the MNV RNA with an AP1 RNA sequence (see Weiss et al.) cloned into it (SEQ ID No. 3). The cloned MNV RNA is referred to as the PrP amplibody (PrP-Amp").

Figure 7:
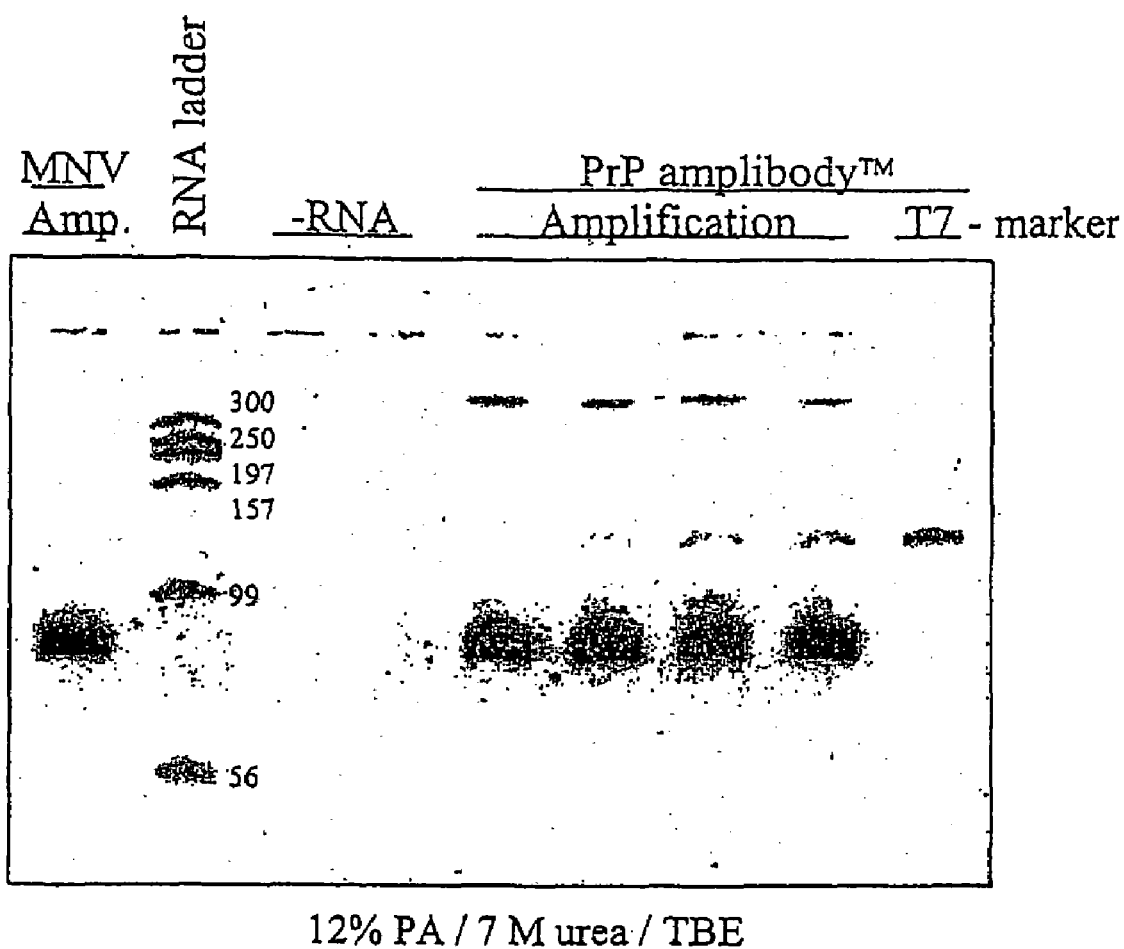
FIG. 7 shows a gel depicting the amplification of MNV (SEQ ID No. 2) and PrP-Amp.

The ability to amplify PrP-Amp was addressed using Q-Amp. Under conditions suitable for amplification, MNV (SEQ ID No. 2) and PrP-Amp were independently subjected to Q-Amp. FIG. 7 presents data demonstrating the along with MNV, PrP-Amp can be amplified by Q-Amp replicase. An example of a suitable protocol for Q-Amp amplification provides a 80 mM Tris-HCl buffer at pH 7.5 together with 20 mM $MgCl_2$, 2 mM dithiothreitol, 200 µM rNTPs, and 200 nM replicase. In a 20 µL reaction, RNA is added and incubated for thirty (30) minutes at 37° C. Under some circumstances, 1 µL [$\alpha$-$P^{32}$] CTP (3000 Ci/mmol) is added to the reaction in order to label the nascent RNAs. Alternatively, detection of amplification products is accomplished by subjecting them to polyacrylamide gel electrophoresis followed by staining the nucleic acids in the gel using, for example, SYBR Gold (from Molecular Probes, Eugene, Oreg.).

Figure 8:
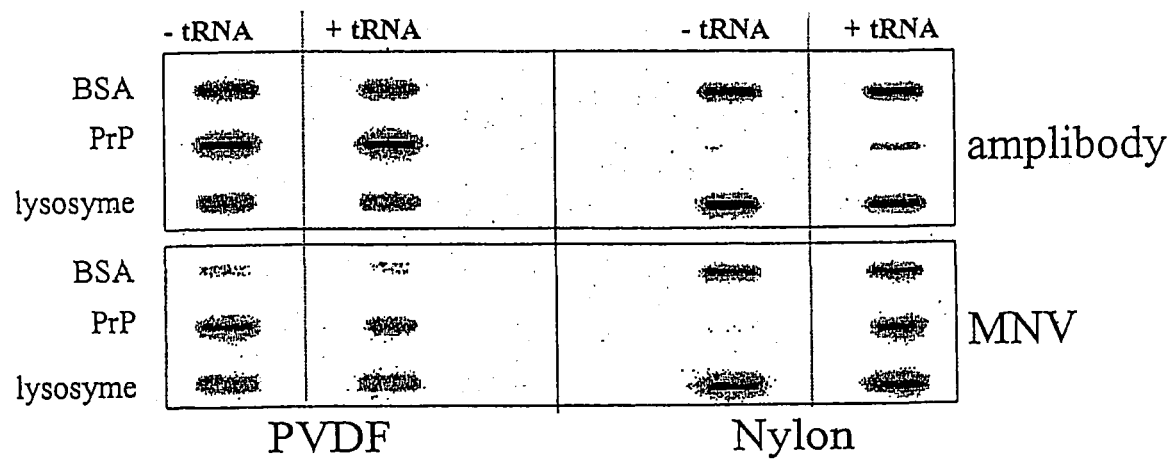
FIG. 8(a) shows a gel demonstrating the specificity of MNV (SEQ ID No. 2) and PrP-Amp binding to a prion protein, (b) represents the same binding data in graphical form.
Figure 8:
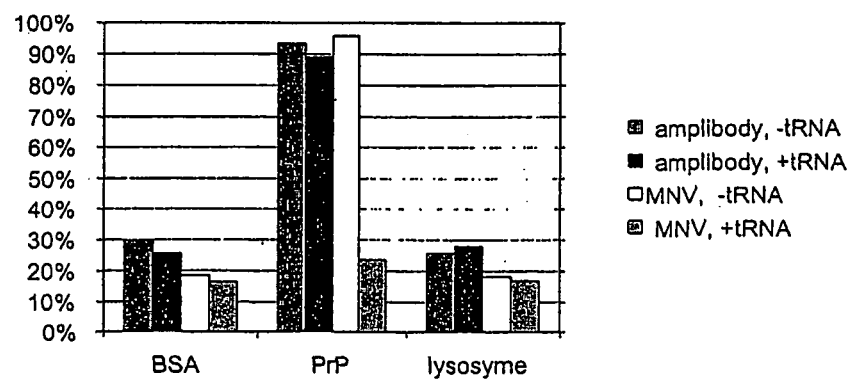

The binding specificity of PrP-Amp was next examined and compared to MNV (SEQ ID No. 2). FIG. 8a shows the binding data. To fully appreciate this figure, it must be realized the reason for using two membranes in this experiment. See Weiss, S., et al., J Virol 1997 November, 71(11): 8790-8797; the entire teachings of which are incorporated herein by reference. Protein and bound RNA will bind to the PVDF membrane. The bound RNA refers to that RNA that is bound to a protein. Free or unbound RNA will pass through the PVDF membrane and bind to the nylon membrane. Therefore, if the RNA is labeled and not bound to protein, then it will pass through the PVDF membrane and a signal will be generated from the nylon membrane where the free-labeled RNA is bound. Conversely, should the labeled RNA bind to a protein, then a signal will be generated from the PVDF membrane. With respect to the PrP-Amp, it can be observed that two signals are visible on the PVDF membrane indicating that this amplibody binds to the prion protein, moreover the presence of tRNA does not affect this binding. Unlike PrP-Amp, binding of MNV (SEQ ID No. 2) to the prion protein is affected by the presence of tRNA. In the presence of tRNA, labeled MNV RNA (SEQ ID No. 2) passes through the PVDF membrane passing onto the nylon membrane indicating the lack of binding to the prion protein in the presence of tRNA. FIG. 8b presents the same data illustrated in FIG. 8a the only difference is that FIG. 8b presents it in a graphical manner. The binding dissociation constant (Kd) presented in Table 1 quantitatively demonstrates that (a) PrP-Amp's binding to the prion protein is independent of the presence of tRNA, whereas, the binding of MNV is drastically reduced in the presence of tRNA, and (b) PrP-Amp has a higher affinity for the prion protein.

TABLE 1

| Description | RNA | Apparent Kd (nM) + tRNA | Apparent Kd (nM) − tRNA |
|---|---|---|---|
| Vector + AP1 (127 nt) | PrP-Amp | 12 | 4 |
| Vector (87 nt) | MNV (SEQ ID No. 2) | 1000 | 38 |

This table clearly shows that the binding of Prp-Amp is very stable, whereas the binding stability of MNV (SEQ ID No. 2) is dependent upon the presence or absence of tRNA.

Figure 9:
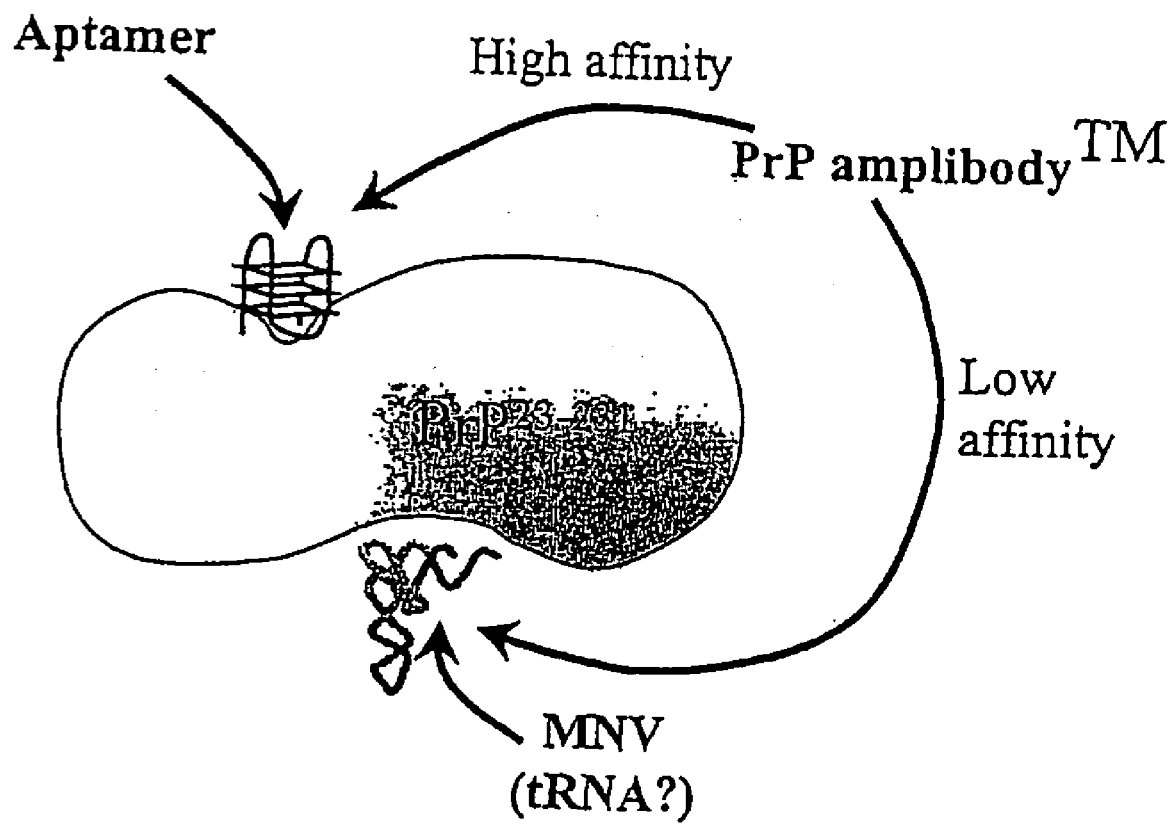
FIG. 9 is cartoon depiction of prion protein's two binding sites.

The binding data presented above suggests that there are at least two types of binding sites on the prion protein. See FIG. 9. First, there is a low affinity site where MNV (SEQ ID No. 2) binds in the absence of tRNA. Then there is the high affinity site where the PrP-Amp binds.

Figure 10:
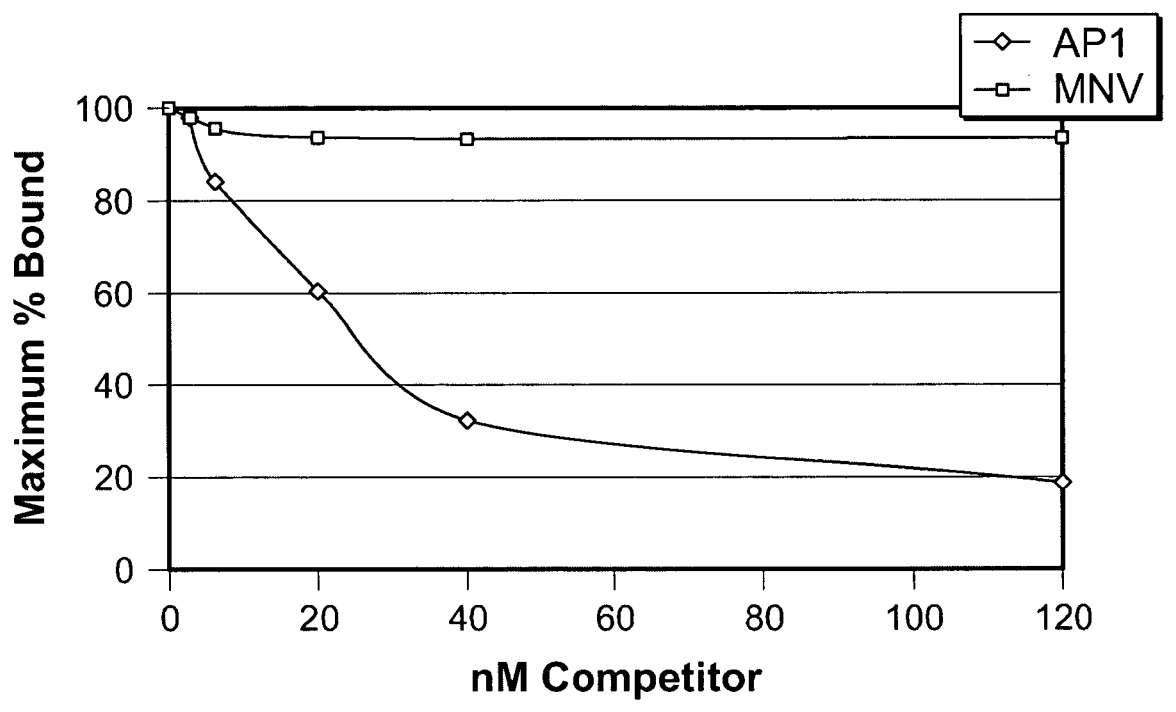

This multiple binding thesis was further examined in a competition study. The binding of PrP-Amp to the prion protein was challenged using either AP1 or MNV (SEQ ID No. 2). FIG. 10 shows that AP1 effectively inhibits PrP-Amp binding, whereas MNV (SEQ ID No. 2) has little or no effect on PrP-Amp's binding. Clearly, then, there must be at least two types of RNA binding sites on the prion protein.

Using tRNA as an instrument to discriminate between binding sites, other RNAs were examined for their binding affinity to the prion protein in the presence of tRNA. The summary of the findings is presented in Table 2.

TABLE 2

| RNA | Apparent Kd (nM) + tRNA |
|---|---|
| RQ11 + 12 (SEQ ID No. 6) | 98 |
| MDV (SEQ ID No. 1) | 167 |
| RQT157 (SEQ ID No. 10) | 185 |
| BS1577 (SEQ ID No. 9) | 2500 |

Based upon the favorable Kd value for RQ11+12 (SEQ ID No. 6), the binding to the prion protein in the presence or absence was then assessed. Table 3 presents this data. It can be appreciated by the data presented in Table 3 that the binding of RQ11+12 (SEQ ID No. 6) to the prion protein in the absence of tRNA is about 4-fold tighter as when compared to binding in the presence of tRNA.

TABLE 3

| RNA | Apparent Kd (nM) + tRNA | Apparent Kd (nM) − tRNA |
|---|---|---|
| RQ11 + 12 (SEQ ID No. 6) | 98 | 26 |
| PrP-Amp | 12 | 4 |

Figure 11:
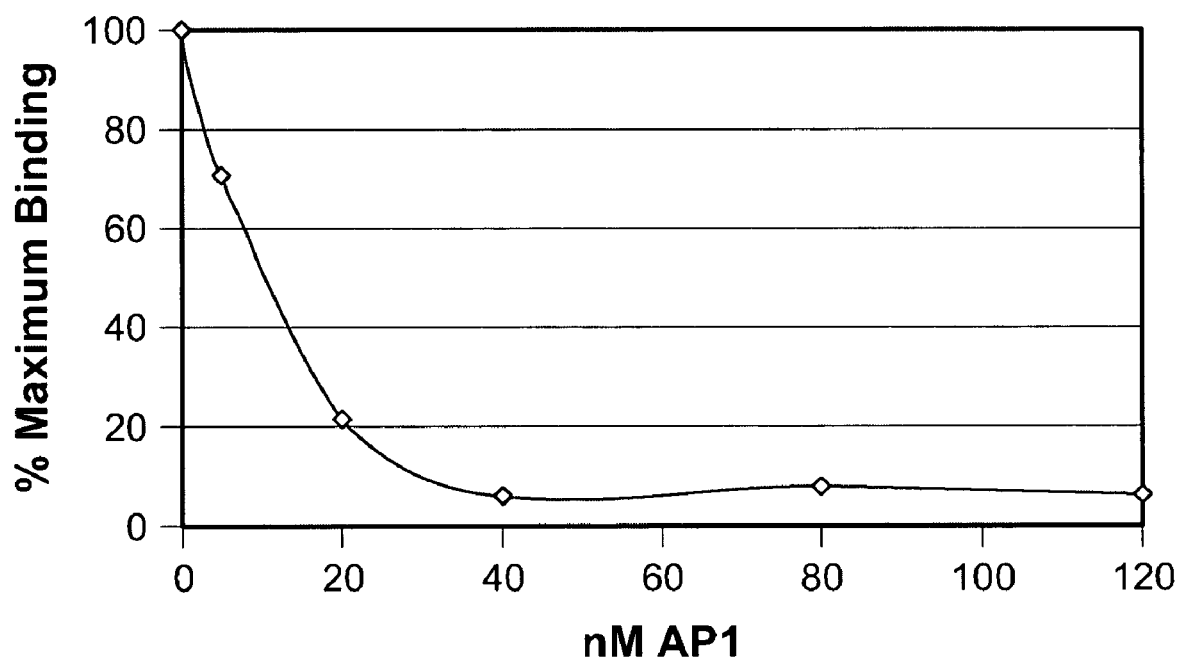
FIG. 11 is a graph showing competition binding data between RQ11+12 (SEQ ID No. 6) and AP1.

To further investigate the binding of RQ11+12 (SEQ ID No. 6), AP1 RNA was used to compete with RQ11+12's (SEQ ID No. 6), binding to the prion protein. FIG. 11 shows that AP1 can effectively inhibit RQ11+12's (SEQ ID No. 6), binding. This data also suggests that RQ11+12 (SEQ ID No. 6), is binding to the high affinity site of the prion protein.

The data thus far presented suggests that binding to the high affinity site requires the presence of a specific RNA structural element. In order to determine the RNA structural elements for stable binding to the high affinity site (in the presence of tRNA), the inventors examined the binding of other RNAs to the prion protein. RNAs from MNV were chosen for this experiment. The TV derivatives contained a random insert of 20 nucleotides. Table 4 presents the data obtained from the experiment. From the data, it can be appreciated that there is a large variation in binding to the high affinity site between RNAs of equal length but of different secondary structure. Presumably, variance in the structure of a single stem accounts for the difference in binding to the high affinity site. Therefore, there appears to be specific RNA structural elements that engender tight binding to the high affinity site.

TABLE 4

| RNA | Apparent Kd (nM) + tRNA |
|---|---|
| MNV-1 (MNVUP) (SEQ ID No. 4), | 217 |
| MNV-2 (MNVLO) (SEQ ID No. 5), | 1667 |
| MNV (SEQ ID No. 2), | 1000 |

Methods of the present invention are directed towards detecting the presence or absence of one or more agglomeration proteins within a sample matrix. An affinity complex is formed by contacting the sample matrix with one or more probes of the present invention. The term "contacting" herein refers to a bringing together of two or more items in a manner consistent with forming an admixture. The probes of the present embodiment comprise the amplibodies of the instant invention.

As used herein, "sample matrix" includes any sample that contains proteins. For example, blood, urine, other bodily fluids, cells, cell extract, tissue and tissue extract (especially neurological tissue) are within the scope of this invention.

Amplibody probes of the present method comprise one or more nucleic acid amplibody molecules having affinity for at least one agglomeration protein. In one embodiment, the RNA polynucleotide component is a naturally or non-naturally occurring molecule with twenty or more ribonucleotide bases. At least one nucleotide sequence portion of this RNA molecule has affinity to at least one consensus sequence present in the agglomeration RNA-binding protein. In this embodiment, the portion of RNA having affinity for agglomeration proteins is a sequence that is derived from either an RNA virus, an RNA phage, a mRNA, a rRNA, a tRNA, a sequence that is received as a template by one or more RNA dependent RNA polymerases, or a combination thereof.

The amplibody preparation can be a homogeneous collection of amplibody. This homogeneous preparation is analogous to a monoclonal antibody preparation. Alternatively, the amplibody preparation can be heterogeneous which is analogous to a polyclonal preparation of antibody.

The instant method also includes the use of a heterogeneous collection of amplibodies. This collection refers to different amplibodies having affinity for different binding sites on the same or different agglomeration proteins. A heterogeneous collection of amplibodies can be introduced to a sample matrix. Affinity complexes can form between a single agglomeration protein and different amplibodies binding at different sites along the agglomeration protein. Additionally, affinity complexes can be formed between different amplibodies and different agglomeration proteins present within the one sample matrix.

The present method includes the detection of any affinity complex formed. The detection of an affinity complex is indicative of the presence of one or more agglomeration proteins present in the original sample matrix. Detection of the affinity complex can be accomplished by a method selected from the group consisting of mass or density measurement, mass spectrometry, plasmon resonance, optical emission or absorption, fluorescence, phosphorescence, luminescence, chemiluminescence, polarization, refractive index changes, electrical conductivity, radioactivity, viscosity, turbidity, and optical rotation.

One or more of the amplibody probes can be labeled. The label can be bound ionically, covalently, or via adsorption. Preferably, the label is bound covalently to any region of the amplibody polynucleotide comprising the sequence of interest and that does not interfere with binding to an agglomeration protein. The label can include, but is not limited to, radioactive isotopes, such as a radioactive phosphorous atom, affinity reagents, such as biotin, intercalating fluorescent dyes, or a fluroescent moiety attached to the amplibody, phosphorescent dyes or chelates, electrophores for detection by mass spectrometry, chemiluminescent moiety chromophores.

Using a Photodyod Array (PDA) detector, a spectral analysis can be performed without the employment of any label per se. The affinity complex (as well as the amplibody) can be monitored and detected by its unique spectral image using a PDA detector. Separation of free amplibody from complexed amplibody (complexed with agglomeration protein) can be accomplished using methods known to those skilled in the art, for example, employing size-exclusion chromatography, filtration, electrophoresis or alike.

The present invention also pertains to a method for detecting one or more agglomeration proteins within a sample matrix using one or more immobilized amplibody probes. In this embodiment, at least one RNA polynucleotide is immobilized to a solid surface. The immobilized polynucleotide can be an amplibody, alternatively, it can hybridize to a second RNA polynucleotide that is an amplibody. This method also extends to a heterogeneous collection of amplibodies, each amplibody having affinity for a different agglomeration protein, alternatively, each amplibody having affinity for a different site on the same agglomeration protein, or a combination of both In a one aspect of this embodiment, a first polynucleotide (can be either DNA or RNA) that comprises a sufficient sequence for hybridizng, under suitable conditions, to a second polynucleotide (that is an amplibody) is immobilized to a surface. See U.S. Ser. Nos. 08/971,845; 06/016,708; and 08/812,105; the entire teachings of which are incorporated herein by reference. The portion of the first polynucleotide that is used for immobilization is different from the sequence region that is employed to hybridize to the second polynucleotide (or amplibody). In this aspect of the invention, the method can be performed sequentially or as a single step. First, a sample matrix is admixed with an appropriate amplibody mixture, either homogeneous or heterogeous mixture of amplibodies, under conditions suitable for forming an affinity complex by interacting amplibody and agglomeration protein. Following this step, the putative affinity complex can be admixed with the first polynucleotide that is immobilized to a surface under conditions suitable for hybridization between the first polynucleotide and second polynucleotide. Second, a sample matrix is admixed with a hybridization complex formed from the first polynucleotide hybridized to the second polynucleotide, wherein the first polynucleotide is immobilized to a surface. Under these conditions, affinity complex formation occurs with an immobilized amplibody. Preferably, any free affinity complex will eventually become immobilized by the hybridization of the second polynucleotide (amplibody)-agglomeration complex with the immobilized first polynucleotide.

In another aspect of this embodiment, the immobilized amplibody is immobilized to a surface using a region of the polynucleotide not affecting the amplibody's ability to interact with an agglomeration protein. The agglomeration protein directly forms an affinity complex with the immobilized amplibody.

Means of attaching a nucleic acid to a surface support, such as a solid support surface, can be by simple adsorption. Preferably, the attachment is mediated through a covalent bond between the nucleic acid and some chemical moiety associated with the support surface, for example, an amine or carboxyl group, or acrylamide. Chemical crosslinkers can be employed to immobilize a nucleic acid to a surface. An example of such a chemical crosslinker is carbodiimide (such as, 1-ethyl-3,3-dimethylaminopropyl-carbodiimide) which can be used to link the phosphate group on the 5' end of a nucleic acid with an amine group on the surface of a support. Additionally, ionic interactions can also facilitate such immobilization of the nucleic acid. The binding can be direct as between the nucleic acid and surface, or indirect such that an intermediate molecule lies between the nucleic acid and the surface. The intermediate molecule need not have any precise length.

Affinity reagents can also be employed to immobilize nucleic acid to a surface. For example, a nucleic acid carrying avidin or biotin moieties to a surface containing the cognate moiety, will bind the nucleic acid to the surface. Another example of using an affinity-based immobilization technique is to coextensively link the nucleic acid of interest to an affinity ligand, for example, biotin or avidin. The cognate receptor to the ligand, for example, if biotin is the ligand, then avidin will be the cognate receptor, will have attached to it a magnetic particle. When a magnetic field is applied to the surface, the magnetic particle, along with what is attached thereto, will be immobilized to the surface.

The support matrix can be a chromatographic support in the form of beads or particles, dipsticks, fibers, containment vessels, thin-layer plates, membranes, gels like polyacrylamide, starch, agarose, cellulose or other polymeric gels.

A kit for determining the presence or absence of one or more agglomeration proteins within a sample matrix is also disclosed herein. The kit comprises one or more amplibody probes. These probes comprise a non-naturally occurring RNA with twenty or more nucleotides, wherein at least one sequence portion of the nucleotides has affinity for the agglomeration proteins. In one embodiment, the affinity sequence portion of the amplibody is derived from either an RNA virus, an RNA phage, a nucleotide sequence that can be received as a template by one or more RNA dependent RNA polymerases, a mRNA, a rRNA, a tRNA, or a combination thereof. In practice, this kit employs the method of the present invention.

In one aspect, the kit has at least two amplibodies, each binding to a different site on the agglomeration protein. At least one amplibody in this embodiment has a label that can be detected via conventional methods. In a particular aspect, one of the amplibodies of the kit is immobilized to a solid support. Other amplibodies in this particular aspect can have affinity for an agglomeration protein and have the ability to hybridize to the immobilized amplibody. In this particular aspect of the invention, preferably the free amplibody is labeled.

The kit can further comprise a means for separating an affinity complex, comprising one or more amplibodies and at least one agglomeration protein, from free amplibody. The separation means can include, but are not limited to, size-based membranes, filtration units, and alike.

Transmissible spongiform encephalopathies (TSEs) are neurodegenerative infectious diseases that affect the central nervous system (CNS). TSEs include scrapies in sheep, Bovine Spongiform Encephalopathy (BSE) in cattle and Cruetzfeld-Jakob Disease (CJD), Guerstmann-Sträussler-Scheinker Syndrome (GSS), kuru, and Fatal Familial Insomnia (FFI) disease in humans (Prusiner, 1982). Common to all of these fatal diseases are long incubation periods and the accumulation of amyloid-like rods or scrapie associated fibrils (SAFs). The formation of SAFs is the result of extensive fibrillation of $PrP^{SC}$, the isoform of the endogenous and innocuous $Prp^C$ protein that is associated with infectivity. The structural transformation of the soluble $PrP^C$ to the insoluble $PrP^{Sc}$ isoform marks the onset and progression to clinical prion disease.

The gene that encodes $PrP^C$ is highly conserved and constitutively expressed from the prnP locus as a 35 kDA glycoprotein (Chesebro et al., 1985 Nature 315:331-33; Oesch et al., 1985 Cell 40:735-46; the entire teachings of which are incorporated herein by reference). Approximately one half of translated $PrP^C$ is processed to the extracellular membrane where it is anchored to the plasma membrane by a C-terminal glycosyl-phophatidyl-inositol (GPI) anchor. However, $PrP^C$ has also be found in two trans-membrane forms, one with the N-terminus inside the ER lumen ($Prp^{Ntm}$; 40-50%,) and the other in the opposite orientation with the C-terminus inside the ER lumen ($PrP^{Ctm}$; 10%). It is unknown if these processing differences reflect the functional properties of these $PrP^C$ forms.

PrP proteins have interesting structural characteristics, particularly the extraordinary transformation from its native, wildtype conformation $PrP^C$ to the infectious $PrP^{Sc}$. The alteration in protein structure is marked by a transition from alpha-helix rich of $PrP^C$ into beta-sheet rich regions in the C-terminal domain of the isoform associated with infectivity (Pan et al., 1993 PNAS, USA 90:10962-66; the entire teachings of which are incorporated herein by reference). Several biochemical traits distinguish the isoforms such as the insolubility of $PrP^{Sc}$ in physiologic solutions and the resistance of its C-terminal domains (amino acids 90-231) to digestion by proteinase K. The structure of the non-protease treated full-length N-terminus of PrP is very flexiable and without a single, stable structure based on NMR structural studies. Therefore, this region of PrP is most likely indistinguishable between the cellular and scrapie isoforms.

The binding of PrP to nucleic acids has been demonstrated many times through the observation of direct complex formation in vitro with purified protein and by copurification of nucleic acids from scrapie associated fibrils (SAFs) removed from infected tissue (Merz et al., 1981 Acta Neuropathol (Berl) 54(1):63-74; the entire teachings of which are incorporated herein by reference). For example, several thousand bases of the viral RNA genome of IAP were co-purified with SAF from infected tissue (Murdoch, et al., 1990 Virology 64(4):1477-86; Akowitz et al., 1994 NAR 22(6):1101-07; the entire teachings of which are incorporated herein by reference). Such observations influenced studies to explore the possibility that nucleic acids were a required genetic component in the transmission of TSE, although no such genetic link has been experimentally determined to date. Indirect evidence for an in vivo association between PrP and viral components is the observation that the rate of $PrP^{Sc}$ formation is accelerated in cells affected with moloney murine leukemia virus (Carp et al., 1999 J Gen Virol 80(Pt 1):5-10; the entire teachings of which are incorporated herein by reference). There is further evidence of interactions between PrP and viral nucleic acids derived from in vitro studies that used recombinant, mammalian PrP proteins expressed in E. coli. Syrian Golden Hamster recombinant $PrP^C$ (srPrP) has a surprising homology of in vitro activities with the nucleocapsid protein from HIV (Ncp7) (Tanchou et al., 1995 J Mol Biol 252:563-71; Gabus et al., 2001a J Mol Biol 307(4):1011-21; Gabus et al., 2001b J Biol Chem 276(22):19301-9; the entire teachings of which are incorporated herein by reference). srPrP has virtually the same level of activity as Ncp7 in the processes of DNA strand-transfer, nucleic acid chaperoning, HIV-RT priming, and the formation of condensed protein/nucleic acid structures. Double stranded DNA also induced the formation of similar condensed PrP structures, as well as resistance to proteinase K digestion (Nandi 1998 Arch Virol 143(7):1251-63; Nandi and Leclerc, 1999 Arch Virol 144(9):1751-63; Nandi and Sizaret, 2001 Arch Virol 146:327-45; the entire teachings of which are incorporated herein by reference). Recently, two small RNA aptamers have been isolated based on their ability to bind to PrP proteins. One aptamer, AP1 (29 nt), was isolated using recombinant srPrP, and is predicted to fold into a compact structure containing three stacked G-quartets, a structure suggested to be important in binding to srPrP (FIG. 12a; Weiss et al., 1997 J Virol 71(11):8790-97; the entire teachings of which are incorporated herein by reference). Using a series of srPrP truncations, the authors localized the binding of AP1 to the flexible N-terminus, within amino acids 23-39.

The specific mechanisms of initiation and progression of prion fibrillation are not well understood. Previous studies have tried to determine if RNA or DNA play a genetic role in the transmission of prion disease (Akowitz et. al. 1994; Nandi and Leclerc, 1999; Cordeiro et. al., 2001 J Biol Chem 276(52):49400-09; Narang 1998 Res Virol 149(6):375-82; Narang 2002 Exp Biol Med 227(1):4-19; the entire teachings of which are incorporated herein by reference).

The inventors conducted a study focusing on the physical interactions and effects of RNA binding to hrPrP. The experiment is presented below in the Example.

The features and other details of the invention will now be more particularly described and pointed out in the examples. It will be understood that the particular embodiments of the invention are shown by way of illustration and bot as limitations of the invention. The principle features of this invention can be employed in various embodiments without departing from the spirit and scope of the invention.

EXAMPLE

The specific mechanisms of initiation and progression of prion fibrillation are not well understood. Previous studies have tried to determine if RNA or DNA play a genetic role in the transmission of prion disease (Akowitz et. al. 1994 NAR 22(6):1101-07; Nandi and Leclerc, 1999 Arch Virol. 144(9):1751-1763; Cordeiro et. al., 2001 J. Biol. Chem 276(52):49400-49409; Narang 1998 Res. Virol. 149(6):375-82; Narang 2002 Exp. Biol. Med. 227(1):4-19; the entire teachings of which are incorporated herein by reference). In this study, the inventors focused on the physical interactions and effects of RNA binding to hrPrP, not the genetics of prion transmission. For this, they used small RNAs of defined sequence to characterize the RNA-binding activities of recombinant human PrP (hrPrP) in vitro. The results obtained demonstrate that hrPrP has high affinity for small RNA species that resides in amino acids 23 to 90 (the N-terminus). The extent of complex formation between PrP and RNA is demonstrated by protection of the RNA species from degradation by RNaseA. They also identified a class of RNAs that tightly bind to hrPrP in the presence of a vast excess of non-specific competitor RNAs.

RQ11+12 (SEQ ID No. 6), a newly described RNA that belongs to this class, also showed the ability to bind specifically to endogenous PrP in mouse brain homogenates and generate RNA-PrP complexes.

The transcription reagents used for this study (T7 RNA polymerase, RNase inhibitor, rNTPs, buffers) were either from Ambion (Austin, Tex.) or MBI Fermentas (Hanover, Md.). Ultra-pure BSA and Nuc-Away spin columns was also from Ambion while Schleicher and Scheull 0.45 μM BA85 nitrocellulose membranes were supplied by VWR (Bridgeport, N.J.). Perlin Elner (Boston, Mass.) supplied the PVDF and Nylon membranes as well as all radioisotopes. The nucleic acid intercalating dyes RiboGreen and SYBR Gold, used for analysis and RNA quantitation were from Molecular Probes (Eugene, Oreg.). General salts, buffers and electrophoresis products were supplied by VWR and Sigma (St. Louis, Mo.). Recombinant human PrP$^{23-231}$, PrP$^{23-144}$, PrP$^{90-231}$ were kindly provided by Man-Sun Sy, Case Western University.)

Homogenates were prepared from whole mouse brains. Ten percent (wt/vol) brain homogenates from wildtype mice and PrP knockout mice (PrP$^{0/0}$) were prepared as follows. Brains were homogenized in nine volumes of PBS supplemented with 0.5% Nonidet P-40, 0.5% deoxycholic acid and a cocktail of protease inhibitors (Sigma). After centrifugation (12,000×g for 30 minutes), the supernatants were aliquoted and stored at −70° C. The protein concentration was measured by Bradford assay, using Pierce reagents supplied by VWR.

Construction of RNAs:

RNAs were synthesized using T7 RNA polymerase and PCR-generated DNA templates. PCR templates were made from either sequenced plasmids or synthetic oligonucleotides using primers that add the T7 polymerase promoter to the 5' end and define the 3' end by run-off transcription. All DNA cloning steps used in the preparation of plasmid templates followed standard molecular biology techniques (Sambrook et al, 1989 Molecular Cloning: A Laboratory Manual. Cold Springs Harbor Laboratory Press, Cold Springs Harbor, N.Y.; the entire teaching of which is herein incorporated by reference). DNA cloning typically involved the annealing of synthetic oligonucleotides, followed by their ligation and cloning into pUC19. RNAs internally labeled were made by the incorporation of [α-$^{32}$P] GTP or CTP at varying specific activities, dependent upon the application. All of the RNAs used in this study were gel purified from 12% poly-acrylarnide/7M urea denaturing gels and then the RNA was collected using an IBI V-channel electroelution apparatus. Prior to gel purification, radiolabeled transcription reactions were prepared using Nuc-Away spin columns (Ambion) while unlabelled reactions were prepared by phenol:chloroform extraction, ethanol precipitation and resuspension in TE (10 mM Tris-HCl, pH 7.4, 1 mM EDTA). The concentration of RNA was measured either as a function of isotope incorporation with a BioScan XER-2000 or by a RiboGreen (Molecular Probes) fluorescence-binding assay using a Sequoia-Turner Model 450 flourometer.

The nucleotide sequences and predicted secondary structures of MDV, MNV (Preuss et al., 1997 J. Mol Biol., October 31, 273(3):600-13; the entire teaching of which is incorporated herein by reference) and AP1 (Weiss et al., 1997 J Virol, November 71(11):8790-8797; the entire teaching of which is incorporated herein by reference) have been reported elsewhere. The following RNAs, shown in the 5'->3' orientation, are described for the first time:

```
(1) AP46 (AP1 with one G-quartet
removed)
5' GGGAAUUUGAGGACGAUGGUAAGUGG 3';    (SEQ. ID NO 7)

(2) AP49-(AP1 with one G-quartet
replaced)
5' GGGAAUUUGAGGAACGAUAGGUAAGUGGA 3'; (SEQ ID NO 8)
BS1577 (non-specific RNA;
contains the sequence for (3) below;

(3) 1577 region of Bacillus subtilis
23S rRNA Ash and Collins, 1992)
5'GGCCCCGUAACUUCGGGAGAAGGGGUGCUCUGUU (SEQ ID NO 9)
AGGGUGCAAGCCCGAGAGAGC 3';

(4) RQT157 (Q-beta replicase vector
RNA)
5'GGGGUUUCGAACCGGAAUUUGAGGGAUGCCUAGG (SEQ ID NO 10)
CAUCCCCCGUGCGUCCCUUUACGAGGGAUUGUCGAC
UCUAGAGGAUCCGGUACCUGAGGGAUGCCUAGGCAU
CCCCGCGCGCCGGUUUCGGACCUCCAGUGCGUG UU
ACCGCACUGUCGACCC 3';
```

(5) RQ11+12 (SEQ ID No. 6) (Q-beta replicase template containing HIV-Rev binding element (underlined)(Iwai et al., 1992), and the Sarcin/Ricin cleavage domain (italicized) (Endo and Wool, 1982)

```
5'GGGGUUUCCAACCGGAAUUUGAGGGAUGCCUAGGCAUCCCCCGUGCGU
CCCUUUACGAGGGAUUGUCGACUCUAGAGUCGACGUCUGGGCGAAAAAUGUA
CGAGAGGACC UUUUCGGUACAGACGGUACCUGAGGGAUGCCUAGGCAUC
CCCGCGCGCCGGUUUCGGACCUCCAGUGCGUGUUACCGCACU
GUCGACCC 3';

(6) MNV:AP1 (SEQ ID No. 3) (AP1 italicized) in MNV
vector RNA)
5'GGUUCAUAGCCUAUUCGGCU UCGCGCAUGGGAAUUUGAGGGACGAUG
GGGAAGUGGGAGCGCGUUUUAAAGGACCUUU UUCCCUCGCGUAGCUAGC
UACGCGAGGUGACCCCCCGAAGGGGGUGCCCC 3';

(7) MNVLO (SEQ ID No. 5) (Q-beta replicase template
RNA)
5'GGGUUCAUAGCCUAUUCGGCUUCGCGCC CCUGGGGUUUGCCUCAGGA
GCGCGUUUUAAAGGACCUUUUUCCCUUGCGUAGCUAGCUACGCGAGGUGA
CCCCCCGAAGGGGGUGCCCC 3';

(8) MNVUP (SEQ ID No. 4) (Q-beta replicase template
RNA)
5'GGGUUCAUAGCCUAUUCGGC UUCGCGCCCGUUUAUAAUACUUAGUGA
GCGCGUUUUAAAGGACCUUUUUCCCUCGCGUAGCUAGCUACGCGAGGUGA
CCCCGAAGGGGGUGCCCC 3'.
```

Filter Binding Assays:

The binding affinity of hrPrP for various RNA ligands was determined by a two-filter binding method essentially as described (Lochrie et. al., 1997 NAR 25(14):2902-10; Battle and Doudna, 2001 RNA 7:123-32; the teachings of which are incorporated herein by reference). Internally labeled RNA, at a concentration always at least ten-fold lower than protein concentration (typically 50 pM), was incubated with increasing amounts of hrPrP in 20 μL-100 μL reactions in Binding Buffer (10 mM Tris-OAc, pH 7.5, 2 mM MgCl$_2$, 250 mM NaCl, 1 μg/μL BSA and 2 mM DTT) for 30 minutes at 37° C. When present, tRNA was at a concentration of 10 ng/ul (~400 nM). Unlabelled RNAs (tRNA, competitor RNAs) were incubated for 15 minutes with hrPrP prior to the addition of any labeled RNAs. After binding RNA to protein, the reactions were vacuum filtered through a protein binding membrane (PVDF or nitrocellulose) and then a nucleic acid binding membrane (positively-charged Nylon) using a Schleicher and Schuell Minifold II Slot Blot hybridization apparatus. A reaction with no protein was also incubated and filtered in order to determine the amount of RNA that binds to the filter in absence of protein. The filters were imaged using a Molecular Dynamics Storm 820 phosphor imager and the program ImageQuant. After subtraction of background values, the percent of RNA bound to the PVDF or nitrocellulose filter in a protein-dependent manner was determined by dividing the intensity of the signal from the protein-binding filter by the sum of the intensity of signal from both filters. The percent of input RNA bound was calculated as an average of at least three measurements at each hrPrP concentration. The average standard deviation was always less than 2% of the input RNA. The percentage of RNA bound to protein was plotted against the concentration of the protein using Microsoft Excel. The apparent $K_d$ is defined as the protein concentration at which 50% of maximal RNA binding occurs.

Gel Shift Assays:

The tRNA gel shift experiments were done in Binding Buffer B at 37° C. for 30 minutes. As above, the competitor tRNA was preincubated for 15 minutes in reactions that contain hrPrP. A 2 µL of sample buffer (30% gylcerol, 0.01% xylene cyanol/bromophenol blue) was added to each sample prior to loading onto a 6% poly-acrylamide/TBE gel run in a 4° C. cabinet. The gels were dried and visualized by autoradiography.

The gel shift experiments using mouse extracts assays were carried out by incubating 50 femtomoles of either $^{32}$P-lablled, gel-purified MNV (SEQ ID No. 2) or RQ11+12 (SEQ ID No. 6) in a total volume of 20 µL in retardation buffer (50 mM MOPS, pH7.4, 5 mM MgCl$_2$, 50 mM LiCl, 1 mM DTT, 1 µg tRNA and 1 µL bovine serum (Invitrogen) in 0.05% deoxycholic acid and 0.05% NP-40). To the RNA and buffer, either hrPrP, brain extract from wildtype mouse, or brain extract from a PrP$^{O/O}$ knockout mouse was added. Reactions were incubated for 20 minutes at room temperature, and then the samples were loaded on 6% polyacrylamide gel containing 4M urea. Electrophoresis was run for 35 minutes at room temperature in TBE buffer (50 mM Trisborate, pH 8.3, 1 mM EDTA). The gel was dried and exposed to x-ray film or analyzed by phoshpor image analysis.

RNaseA Protection Assay:

Reactions (20 µL) were incubated for 30 minutes at 37° C. in 10 mM Tris-HCl, pH 7.4, 100 M NaCl, and 1 ml EDTA. The concentration of RNA was 500 pM where indicated and the concentration of hrPrP was 20 nM when present. After 30 minutes, the concentrations of the reactions were adjusted to 1 pg/µL RNaseA where indicated. After an additional 15 minutes at 37° C., an equal volume of loading buffer was added (94% formamide, 40 mM EDTA, 0.001% bromophenol blue/xylene cyanol), the samples immediately heated to 95° C. for 3 minutes, and then immediately separated on a 6% PA/7M urea/TBE denaturing gel. Image analysis was done using a Molecular Dynamics Strom 820 Phosphorimager.

Small RNAs Bind to hrPrP In Vitro:

Stable complex formation between PrP proteins and nucleic acids has been demonstrated many times both with recombinant and native PrP$^C$ in vitro (Nandi 1998, Arch Virol. 143(7):1251-63; Nandi and Leclerc, 1999, Arch Virol. 144(9):1751-63; Nandi and Sizaret, 2001, Arch Virol. 146: 327-45; Weiss et al., 1997, J. Virol 71(11):8790-97; the teachings of which are incorporated herein by reference) and PrP$^{Sc}$ in vivo (Merz et al., 1981, Acta Neuropathol (Berl). 54(1):63-74; Murdoch, et al., 1990, Virology 64(4):1477-86; Akowitz et al., 1994, NAR 22(6):1101-07, the teachings of which are incorporated herein by reference). In this study, they further characterized the RNA binding activity of hrPrP with a collection of small, artificial RNAs (56-242 nt). Although not directly relevant to the binding study itself, several of these RNAs have been engineered to be viable templates for exponential amplification by the RNA-dependent RNA polymerase, Q-beta replicase (Preuss et al., 1997, J Mol Biol. 273(3):600-13; the teachings of which are incorporated herein by reference).

The apparent dissociation constants ($K_d$) between the RNAs and hrPrP were determined using a two-filter binding assay (Lochrie et. al, 1997, NAR 25(14):2902-10; Battle and Doudna, 2001, RNA 7:123-32; the teachings of which are incorporated herein by reference). Gel purified RNAs and hrPrP were incubated at 37° C. in a high salt buffer (Binding Buffer A; 2 mM MgCl$_2$, 250 mM NaCl) similar to the one used in the selection of RNA aptamers from a random library with affinity to recombinant syrian golden hamster PrP$^C$ (srPrP) (Weiss et al. 1997). These experiments produced a family of specific PrP-binding RNAs that can be identified by three stacked, G-quartets. In particular, the aptamer AP1 (FIG. 12a) demonstrated the ability to bind specifically to srPrP and the interaction was further localized to the 16 N-terminal amino acids (23-39). The inventors also constructed AP1 and used it as a positive control to evaluate RNA species from our collection. Using their own developed system, the apparent dissociation constant ($K_d$) of AP1 to hrPrP was determined as 5.0 nM (Table 5).

TABLE 5

| RNA | Length (nt) | $K_d$ (nM) + tRNA | $K_d$ (nM) − tRNA | Fold effect |
|---|---|---|---|---|
| MNV:AP1 (SEQ ID No. 3) | 130 | 12 | 3.8 | 3.2 |
| AP1 | 29 | 81 | 5.0 | 16.0 |
| RQ11 + 12 (SEQ ID No. 6) | 197 | 91 | 26 | 3.5 |
| AP46 (SEQ ID No. 7) | 26 | 100 | 14 | 7.1 |
| AP49 (SEQ ID No. 8) | 29 | 161 | 15 | 11.0 |
| MDV (SEQ ID No. 1) | 244 | 170 | 7.6 | 22.0 |
| RQT157 (SEQ ID No. 10) | 157 | 185 | 56 | 3.3 |
| MNVUP (SEQ ID No. 4) | 118 | 220 | 5.0 | 44.0 |
| MNV (SEQ ID No. 2) | 86 | 1000 | 38 | 26.0 |
| MNVLO (SEQ ID No. 5) | 118 | 1700 | 4.4 | 390.0 |
| BS1577 (SEQ ID No. 9) | 56 | 2500 | 31 | 81.0 |

Figure 12:
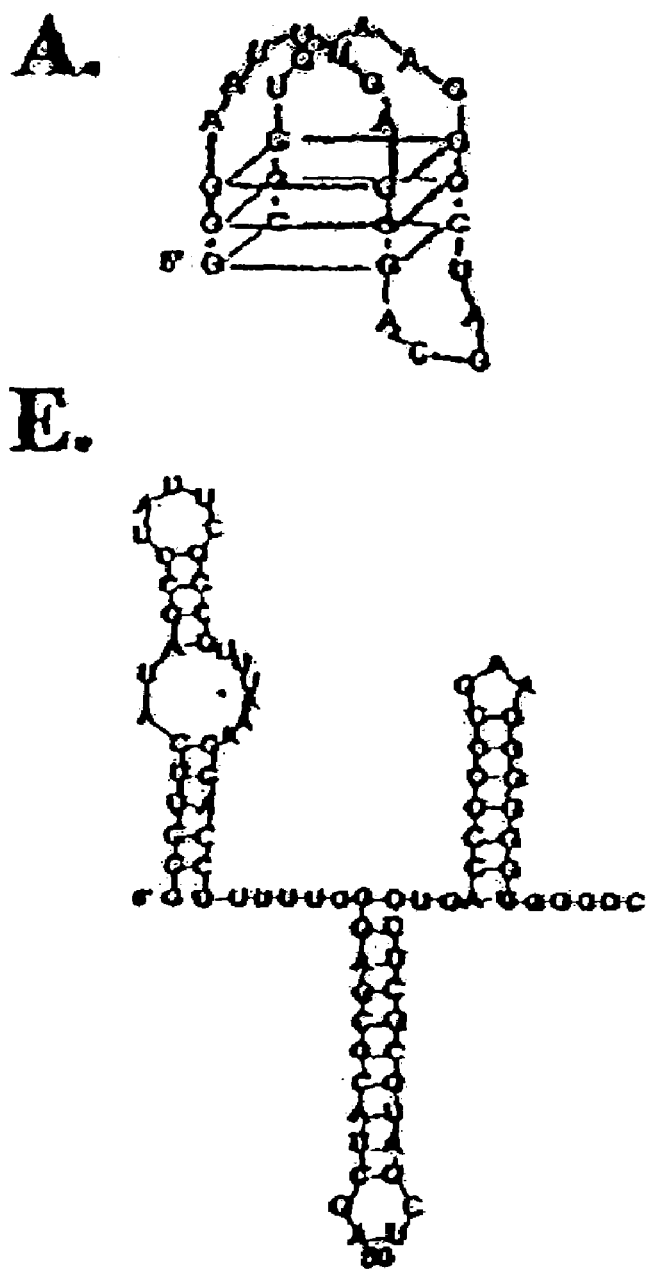
FIG. 12 shows the secondary structure for (a) AP1, (b) nucleotides 22-53 of MNVLO (SEQ ID No. 5), (c) MNVUP (SEQ ID No. 4), (d) BS1577 (SEQ ID No. 9), (e) MNV (SEQ ID No. 2), (f) RQT157 (SEQ ID No. 10) and (g) RQ11+12 (SEQ ID No. 6)
Figure 12:
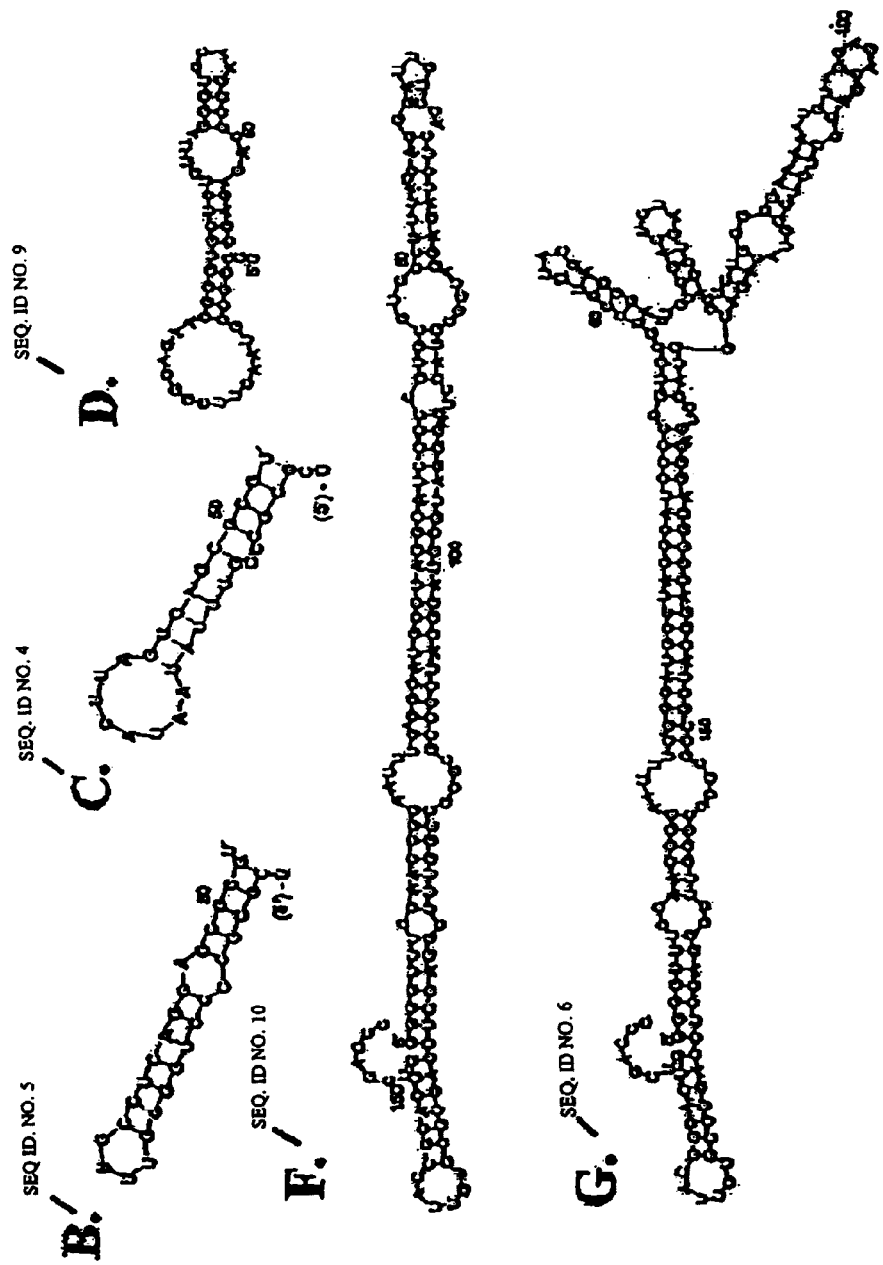

The $K_d$ was then determined between hrPrP and a collection of small RNAs, each predicted to contain a substantial amount of secondary structure (FIG. 12). Reactions were incubated for thirty minutes to ensure equilibrium had been reached (data not shown). Surprisingly, each of the RNAs tested demonstrated a considerable affinity for hrPrP (Table 5). AP46 (SEQ ID No. 7) is AP1 minus one G-quartet while AP49 replaces the first G-quartet in AP1 with the sequence GAAA. MDV (SEQ ID No. 1) and MNV (SEQ ID No. 2), RNAs whose structures have been published previously, are template RNAs for Q-beta replicase (Preuss et. al, 1997). MNVUP (SEQ ID No. 4) and MNVLO (SEQ ID No. 5) are derived from a library that contains 20 random nucleotide inserted into the 5' loop of MNV (SEQ ID No. 2). BS1577 (SEQ ID No. 9) is a small RNA containing the 1577 rRNA region from *Bacillus subtilis* (Ash and Collins, 1992, FEMS Micro. Letters, 94:75-80; the teachings of which are incorporated herein by reference). The tightest binding RNA, MNV:AP1 (SEQ ID No. 3), has a $K_d$ of 3.8 nM and is a composite RNA containing the AP1 aptamer cloned into the Q-beta replicase template RNA MNV (SEQ ID No. 2). MNV:AP1 (SEQ ID No. 3) was developed to investigate its utility as an amplifiable RNA with specificity for hrPrP. It is also easier to generate than AP1 due to its larger size. Another RNA that can be amplified by Q-beta replicase and binds tightly to hrPrP is RQ11+12 (SEQ ID No. 6). RQ11+12 (SEQ ID No. 6) was originally designed for use in the detection of the HIV-1 Rev protein after processing into a bipartite probe by the RNA-cleaving phytotoxin sarcin (Zeiler et. al, 2000, Proceedings of SPIE Aerosense 2000, 4036:103-14; the teachings of which are incorporated herein by reference). For these reasons, one of the stem-loop structures in RQ11+12 (SEQ ID No. 6) contains a consensus sequence for the HIV-1 Rev Binding Element (RBE) (Iwai et. al., 1992, NAR 20(24):6465-72; the teachings of which are incorporated herein by reference) adjacent to the consensus cleavage site for the phyotoxins sarcin and ricin (S/R) (FIG. 12d) (Endo and Wool 1982, J Biol. Chem. 257(15): 9054-60; the teachings of which are incorporated herein by reference). These additional sequences may have something to do with increased binding affinity to hrPrP because RQT157 (SEQ ID No. 10), which is essentially RQ11+12 (SEQ ID No. 6) without the stem-loop containing the RBE and S/R domains, formed the least stable complex with hrPrP, even though it still had an impressive apparent $K_d$ of 56 nM. RQT157 (SEQ ID No. 10) is in turn derived from RQ135, an RNA that is efficiently replicated by Q-beta replicase (Munishkin et. al., 1991, J Mol Bio 221(2):463-72; the teachings of which are incorporated herein by reference).

hrPrP Binding Specificity Can be Differentiated by tRNA:

Because all of the RNAs had apparent dissociation constants with hrPrP measuring below 100 nM, the inventors hypothesized that the binding interaction lacks specificity. To challenge this observation, they assayed the binding affinity of the RNAs in their collection to hrPrP in the presence of purified tRNA, which is sometimes included in RNA binding assays to sequester non-specific binding sites (Battle and Doudna, 2001). However, it is known that the interactions between the anticodon of tRNAs can form very stable complexes with complementary RNAs (Grosjean et. al., 1976, J Mol Bio 103:499-519; the teachings of which are incorporated herein by reference). Therefore, it was first necessary to demonstrate that the tRNA was not binding directly to our test RNAs and inhibiting their binding to hrPrP by sequestering the RNAs.

Figure 13:
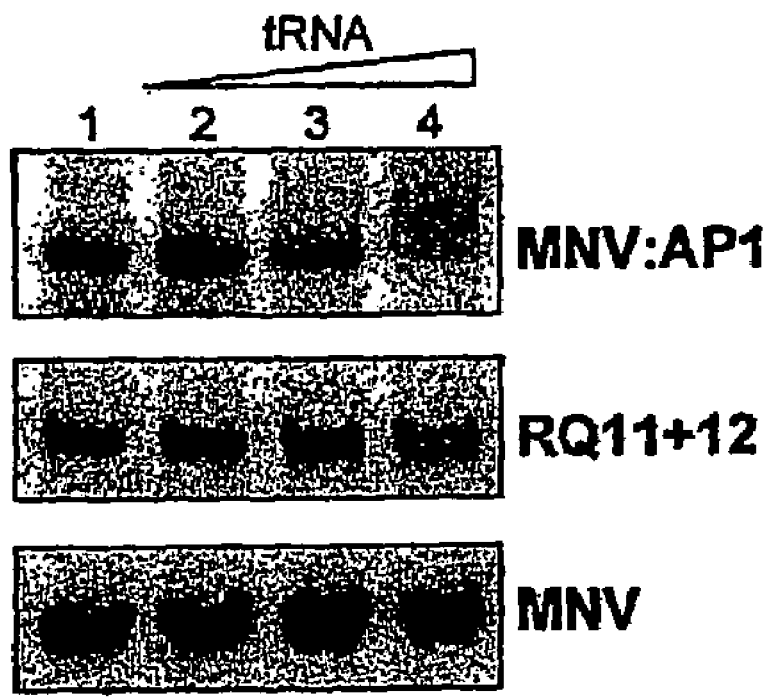
FIG. 13 is an RNA-RNA gel shift.
Figure 14:
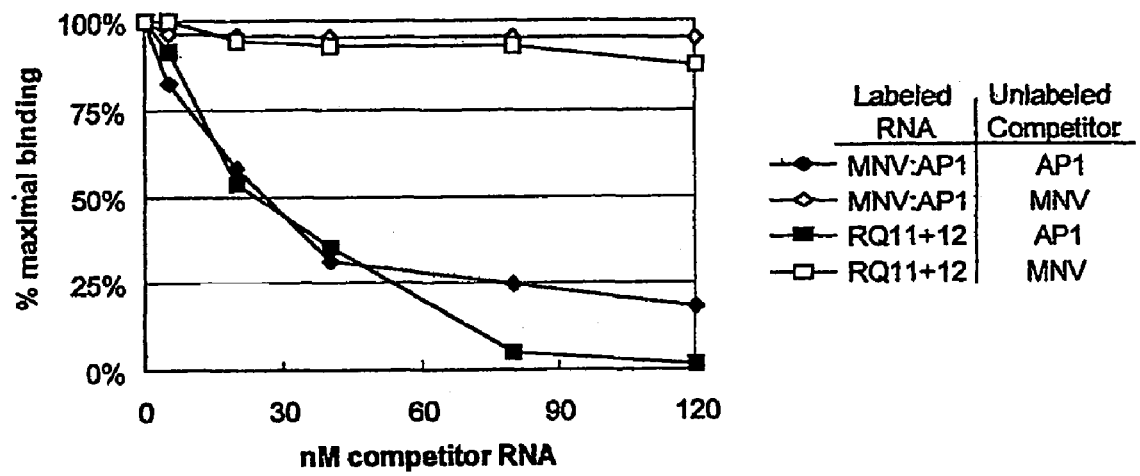
FIG. 14 is a graph showing the results from a competition study of MNV:AP1 (SEQ ID No. 3) and RQ11+12 (SEQ ID No. 6) binding to hrPrP by AP1 and MNV (SEQ ID No. 2)
Figures 15A, 15B:
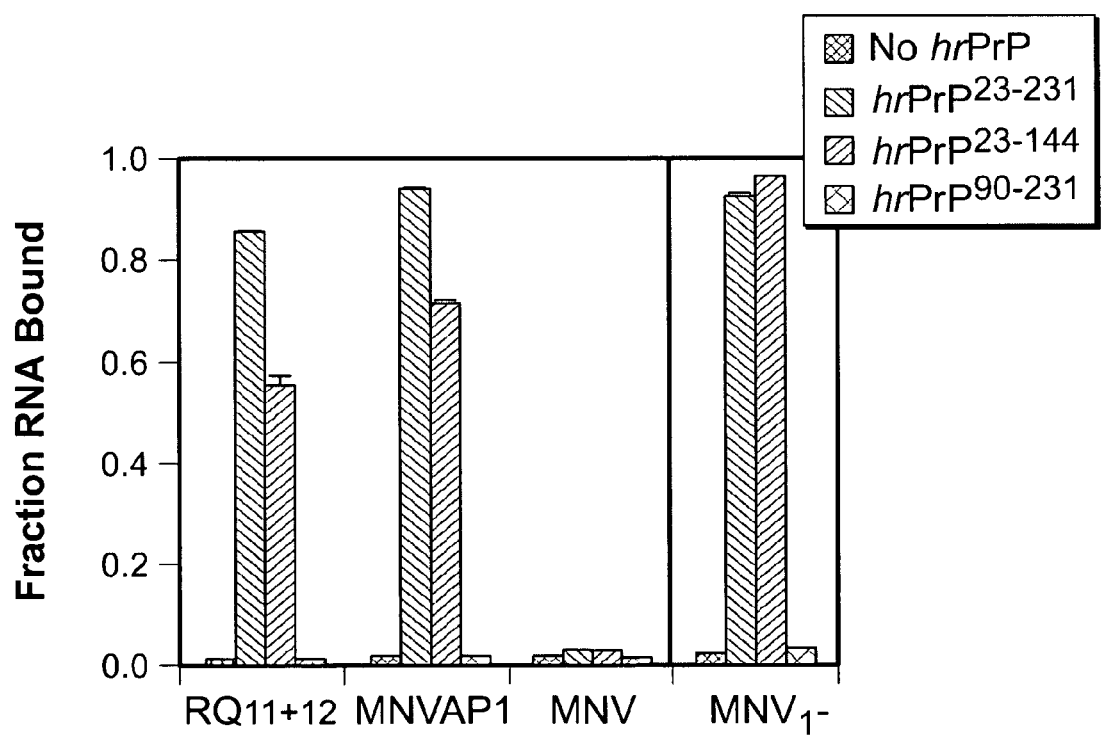
FIG. 15(a) shows the topology of hrPrP, and (b) illustrates graphical data for the binding of RNA to truncated hrPrP.

A gel shift assay was used to determine if complexes would form between tRNA and a subset of their RNA collection (FIG. 13). After a thirty minute incubation at 37° C. in Binding Buffer A, MNV:AP1 (SEQ ID No. 3) migrates predominantly as a single band on a non-denaturing gel (lane 1). Addition of 10 ng/µL or 100 ng/µL tRNA to the incubation did not alter the electrophoretic mobility of MNV:AP1 (SEQ ID No. 3) (lanes 2 and 3). When the tRNA concentration was increased to 1 µg/µL, however, the pattern of MNV:AP1 (SEQ ID No. 3) migration changes, with the appearance of a second, slower migrating band that contains at least half of the RNA present (lane 4). This banding pattern suggests the formation of a I complex between tRNA and MNV:AP1 (SEQ ID No. 3) when tRNA is present at a concentration of 1 µg/µL. In contrast, RQ11+12 (SEQ ID No. 6) and MNV (SEQ ID No. 2) did not form a complex at any of the tRNA concentrations (FIGS. 13b and c). Because there were no interactions at the lower concentration of tRNA, the inventors chose to work at a concentration of 10 ng/µL tRNA as an inhibitor of non-specific RNA interactions. This concentration equates to approximately a 400 nM concentration of tRNA, which will be in vast molar excess over any of the RNAs in the ensuing assays, yet low enough to maintain confidence that inhibition of binding will not be due to sequestration of RNAs.

When the binding of the various RNA species were reexamined in the presence of tRNA, a greater differential in binding affinity was observed (Table 5, column 2). In the presence of the non-specific inhibitor, the measured $K_d$ values ranged from 12 nM to 2500 nM. The RNAs that were minimally affected by the presence of tRNA and maintained $K_d$ values below 100 nM include AP1, the control RNA, as well as MNV:AP1 (SEQ ID No. 3) and RQ11+12 (SEQ ID No. 6). The rest of the RNAs are more severely affected by tRNA, in some cases, by over two orders of magnitude. Several of these RNAs have dissociation constants ($K_d$) measuring in the micromolar range. The competitive binding data suggests that the level of specificity in binding of the RNAs to hrPrP is highly variable. Yet there are few clues as to what generates this level of specificity for RNAs with apparently disparate; structures like RQ11+12 (SEQ ID No. 6) and MNV:AP1 (SEQ ID No. 3). At the very least, this analysis allows one to rule out length and the overall thermodynamic stability of the RNAs as the factors that dictate stable binding to hrPrP in the presence of a vast excess of non-specific competitor RNAs. The effect of RNA secondary structure on hrPrP affinity is underscored by MNVLO (SEQ ID No. 5) and MNVUP (SEQ ID No. 4), which differ only by a small stem-loop structure, yet their $K_d$ values vary over sevenfold (FIGS. 12b and c).

An RNA Family That Engenders High Affinity, Specific Binding to hrPrP:

In an attempt to elucidate the requirements in RNA necessary to be bound by hrPrp with high affinity and specificity, the inventors analyzed a subset of four RNAs that are different in their nucleotide composition and predicted architecture. AP1 was chosen because it binds to the N-terminus PrP (Weiss et. al., 1997). MNV (SEQ ID No. 2) was also chosen because its affinity was greatly affected by the presence of tRNA and therefore represents an RNA that binds in a nondiscriminatory manner to hrPrP. Therefore, MNV (SEQ ID No. 2) is used as an equivalent to non-specific tRNA in the competition experiments because the tRNA used earlier in this study is a heterogenous population and the effect of each tRNA species in binding to hrPrP remains obscure. In particular, it is known that hrPrP has the ability to interact with $tRNA^{Lys}$ (Gabus et al., 2001, J Biol Chem 2001b. Jun. 1, 276(22):19301-9; the teachings of which are incorporated herein by reference). MNV:AP1 (SEQ ID No. 3) and RQ11+12 (SEQ ID No. 6) were chosen because both RNAs are amplifiable by Q-beta replicase, bind specifically to hrPrP with high affinity and were least affected by tRNA.

The binding specificity of these RNA species was challenged in competition; experiments involving radioactively labeled RNAs and unlabeled competitor RNAs (FIG. 14). The binding of labeled MNV:AP1 (SEQ ID No. 3) (50 pM) to hrPrP (50 nM) was examined in the presence of the competitor RNAs AP1 or MNV (SEQ ID No. 2) over a 5 nM to 120 nM range of concentration. In order to assure that the competitor RNA had a chance to interact with hrPrP, it was always added to the reaction 15 minutes prior to the labeled RNA. After a 30-minute incubation, the extent of binding was measured with the two-filter assay. Under these conditions, AP1 effectively inhibited the binding of MNV:AP1 (SEQ ID No. 3). At a concentration of 120 nM AP1, binding of MNV:AP1 (SEQ ID No. 3) was reduced to below 25%. In contrast, when the competing MNV (SEQ ID No. 2) is present at a concentration of 120 nM, binding of MNV:AP1 (SEQ ID No. 3) to hrPrP is reduced by only 5%. This observation would be consistent with a model where 95% of MNV:AP1 (SEQ ID No. 3) binding to hrPrP occurs via the AP1 sequence. These results also suggest that the AP1 sequence and not the MNV sequence (SEQ ID No. 2) is responsible for specific, high affinity binding to hrPrP. Consistent with this conclusion is the measured $K_d$'s for MNV (SEQ ID No. 2) and AP1 in the presence of tRNA (Table 5).

The binding of RQ11+12 (SEQ ID No. 6) to hrPrP was examined using the same experimental approach. The pattern of inhibition of RQ11+12 (SEQ ID No. 6) binding to hrPrP with the same MNV (SEQ ID No. 2) and AP1 competitors is nearly identical to that of MNV:AP1 (SEQ ID No. 3). Both MNV (SEQ ID No. 2) and AP1 inhibit the binding of RQ11+12 (SEQ ID No. 6) to hrPrP slightly more than they do the binding of MNV:AP1 (SEQ ID No. 3) to hrPrP. This observation is consistent with the slightly lower affinity of RQ11+12 (SEQ ID No. 6) to hrPrP as compared to MNV:AP1 (SEQ ID No. 3). This competition data does not prove, but raises the possibility that RQ11+12 (SEQ ID No. 6) and MNV:AP1 (SEQ ID No. 3) share a common mode of binding to hrPrP.

RNAs Bind to the Amino Terminus of hrPrP:

RQ11+12 (SEQ ID No. 6) was chosen for further characterization because it binds to hrPrP with fairly high affinity and it is resistant to non-specific competition from tRNA or MNV (SEQ ID No. 2). In addition, RQ11+12 (SEQ ID No. 6) does not interact with tRNA, even at high concentrations (up to 40 μM), unlike MNV:AP1 (SEQ ID No. 3). Finally, RQ11+12 (SEQ ID No. 6) can be rapidly amplified by Q-beta replicase. After testing several buffers, it was determined that the binding of RQ11+12 (SEQ ID No. 6) to hrPrP in the absence of tRNA was improved almost tenfold ($K_d$=2.2 nM) in 10 mM Tris-OAc, pH 7.5, 100 mM NaCl, 1 mM DTT (Buffer B; data not shown). Binding to hrPrP was also improved for MNV (SEQ ID No. 2) in Buffer B (2.6 nM). Interestingly, in Buffer B, RQ11+12 (SEQ ID No. 6) and MNV (SEQ ID No. 2) have the similar $K_d$ values in the absence of tRNA.

Truncated hrPrP proteins were used to determine the physical location of the RNA binding activity. In addition to the full length recombinant protein, $hrPrP^{23-231}$, the inventors also examined the N-terminal portion ($hrPrP^{23-144}$), and the C-terminal portion ($PrP^{90-231}$) using the filter binding assay in Binding Buffer B in the presence of tRNA (FIG. 15). As expected from the results of the competition experiments, both RQ11+12 (SEQ ID No. 6) and MNV:AP1 (SEQ ID No. 3) bind only to full length hrPrP and the N-terminal truncation (FIG. 16*b*). Because the protein concentration was 20 nM for this set of experiments, MNV (SEQ ID No. 2) was unable to bind to hrPrP in the presence of 10 ng/μL tRNA. However, when tRNA was removed from the binding buffer, MNV (SEQ ID No. 2) binding occurs to either the full length or N terminal portion of PrP. There was no detectable binding of any of the RNAs to C-terminal truncation, $PrP^{90-231}$. This data demonstrates that both the discriminatory and non-discriminatory RNA-binding activities of hrPrP reside in the N-terminus of hrPrP, within amino acids 23 to 90.

Protection From RNaseA Degradation Correlates With Binding:

A ribonuclease protection assay was used to examine the nature of the interaction between hrPrP and RNA. If hrPrP interacts minimally with and does not sequester much of the RNA structure, then the RNA should be susceptible to ribonuclease degradation. However, if the RNA/protein complex involves the whole RNA molecule and the interaction with hrPrP sequesters most of the RNA, then the RNA should be stabilized against ribonuclease degradation.

To examine the hrPrP/RNA complexes, RQ11+12 (SEQ ID No. 6) and MNV (SEQ ID No. 2) were incubated with excess hrPrP and allowed to interact for 30 minutes. RQ11+12 (SEQ ID No. 6) was chosen as, a representative of discriminatory binding, while MNV (SEQ ID No. 2) was chosen to represent non-discriminatory binding. RNaseA was then added and the incubation continued for an additional 15 minutes (FIG. 16). After this treatment, approximately half of the RNAs remained in samples containing hrPrP, while greater than 95% of the RNA degraded in samples containing RNA alone. If tRNA (10 ng/μL) is included in the initial incubation, then the level of protection of MNV (SEQ ID No. 2) imparted by hrPrP is approximately half of that in the absence of tRNA, while the level of protection of RQ11+12 (SEQ ID No. 6) remains unchanged. The pattern of protection of RQ11+12 (SEQ ID No. 6) and MNV (SEQ ID No. 2) directly correlates with their pattern of binding to hrPrP and suggests that complex formation with hrPrP protects bound RNAs.

RQ11+12 (SEQ ID No. 6) Specifically Binds PrP:

Binding studies in solutions of increasing biological complexity were used to investigate the specificity of RQ11+12 (SEQ ID No. 6) binding to PrP. The theoretical isoelectric point of $hrPrP^{23-231}$ is 9.39 (ExPASy molecular biology server, Swiss Institute of Bioinformatics) and therefore the protein carries a positive charge in the conditions of the binding assays. As a consequence of its nucleotide composition, the RQ11+12 (SEQ ID No. 6) RNA is negatively charged. Therefore, the positive charge of hrPrP and the negative charge of RQ11+12 (SEQ ID No. 6) raise the possibility that the binding between RQ11+12 (SEQ ID No. 6) and hrPrP is charge based. To challenge this possibility, the protein lysosyme was used in a binding assay with RQ11+12 (SEQ ID No. 6) because its theoretical pI is 9.9 (ExPASy) and it should also be positively charged under the conditions of the assay (FIG. 17*a*). Assay conditions were manipulated (based on the results in Table 5) such that RNA (2 nM) and protein (20 nM) concentrations would allow extensive binding for RQ11+12 (SEQ ID No. 6), but not MNV (SEQ ID No. 2) (Binding Buffer A in the presence of 10 ng/μL tRNA). In all cases, MNV (SEQ ID No. 2) binding was at background levels. Binding of RQ11+12 (SEQ ID No. 6) to hrPrP was approximately 90% while binding to BSA and lysozyme was at background levels. These results demonstrate that RQ11+12 (SEQ ID No. 6) does not interact non-specifically with the positively-charged lysosyme protein.

The specificity of RQ11+12 (SEQ ID No. 6) for PrP was further confirmed by examining binding in mouse brain extracts using a gel shift assay. Extracts contain a physiological diversity of proteins, which will provide a stringent test of the specificity of RQ11+12 (SEQ ID No. 6) for PrP. After incubation with 40 ng of hrPrP, migration of labeled

Figure 17A:
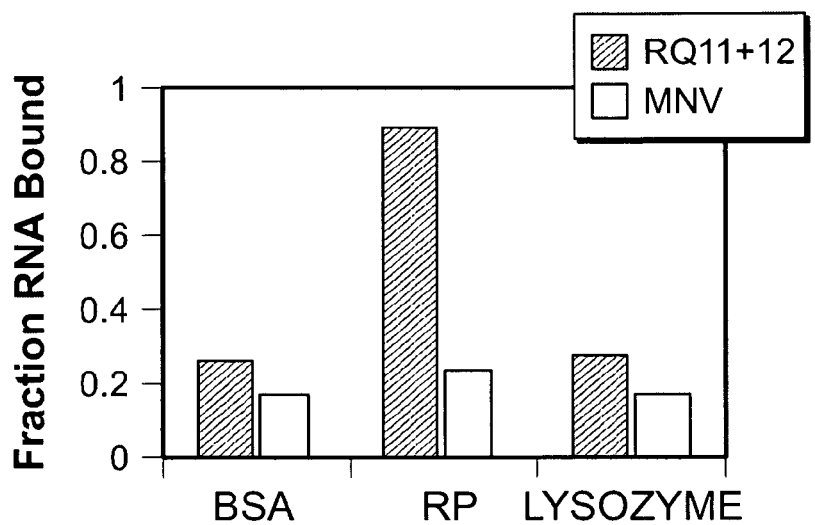
FIG. 17 illustrates data demonstrating that RQ11+12 (SEQ ID No. 6) binds specifically to PrP where (a) shows the results of a filter binding assay, and (b) shows the results of a gel shift assay.
Figure 17B:
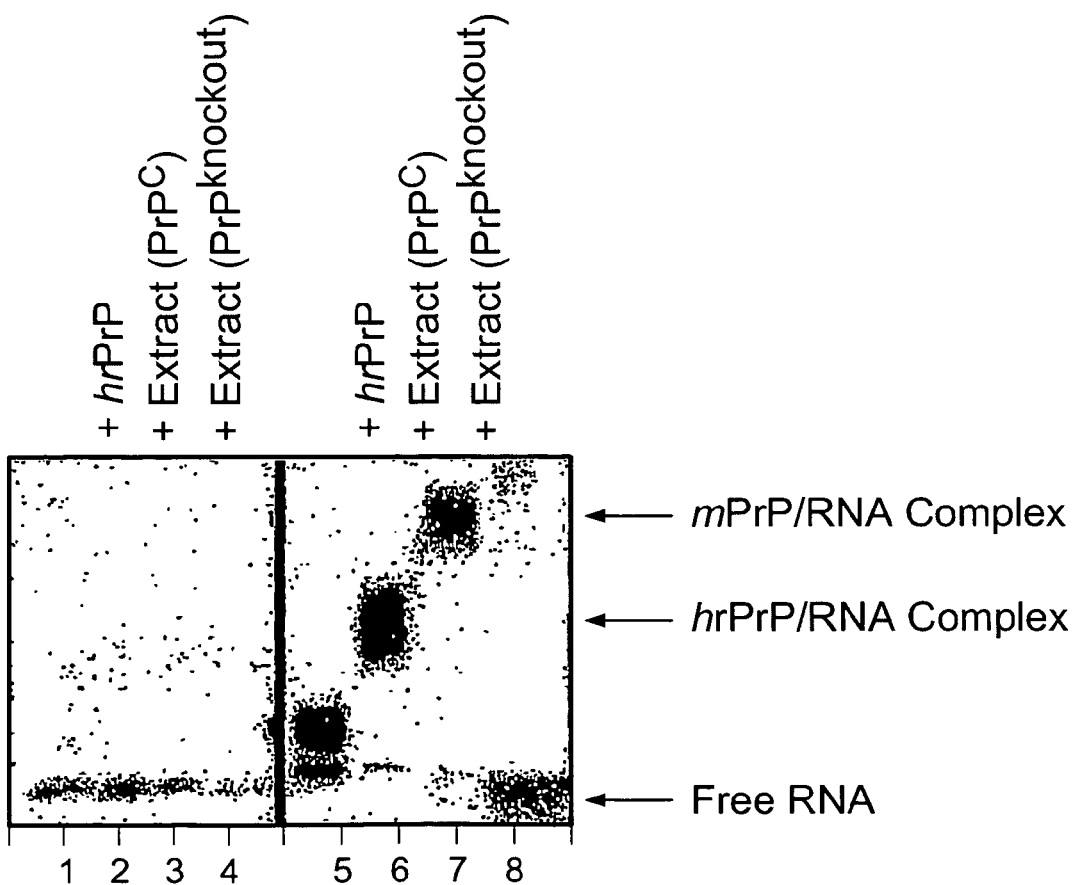

RQ11+12 (SEQ ID No. 6) is retarded through a polyacrylamide gel during electrophoresis while MNV (SEQ ID No. 6) migration is unaffected (FIG. 17b lanes 5 and 6 versus 1 and 2). The specificity of RQ11+12 (SEQ ID No. 6) for PrP is demonstrated after incubation with an equivalent amount (20 μg) of either wildtype mouse brain extract or a mouse PrP-knockout brain extract (lanes 7 and 8). A shift is observed only with the wildtype mouse, implying that the shift observed in lane 7 is due solely to the presence of endogenous PrP present in the wildtype extract. The greater retardation of RQ11+12 (SEQ ID No. 6) in lane 7 than in lane 6 is possibly due to either the post-translational modifications present in native PrP and lacking in hrPrP, the association of $PrP^C$ with host proteins or the presence of PrP dimers that form in vivo and not in purified, recombinant PrP (Yeheily et al., 1997, Neurobiology of Disease 3:339-355; Meyer et. al., 2000, J Biol Chem Dec. 1, 275(48):38081-7; the teachings of which are incorporated herein by reference). The pattern of interaction between the RNAs and native mouse PrP in extracts is reminiscent of the filter binding experiments done in the presence of tRNA where RQ11+12 (SEQ ID No. 6) shows high level specificity and MNV does not.

RQ11+12 (SEQ ID No. 6) Promotes Fibrillation of hrPrP:

In recently published studies, it was reported that DNA can induce the fibrillation of recombinant PrP in vitro (Nandi and LeClerc, 1999). In these experiments, a 1500 nt double stranded DNA, comprised entirely of G-C base pairs (gcDNA), was incubated at low pH (5.0) with purified, recombinant protein. Using the aggregation specific dye Congo Red, the inventors were able to demonstrate DNA-dependent fibrillation. In addition, this PrP/DNA aggregate was resistant to digestion by proteinase K, a hallmark of $PrP^{Sc}$ structural transformation.

Figure 18:
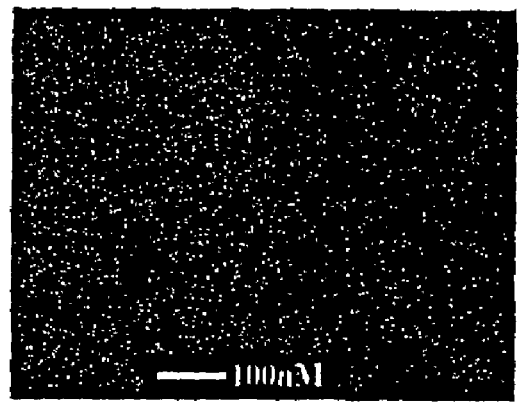
FIG. 18(a) shows an electron micrograph with hrPrP, and (b) hrPrP and RQ11+12 RNA (SEQ ID No. 6).
Figure 18:
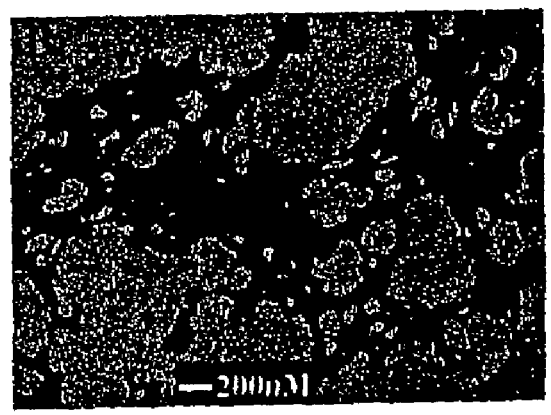

The inventors were interested if RQ11+12 (SEQ ID No. 6) had the same ability. Unlike the gcDNA used in Nandi's studies, RQ11+12 (SEQ ID No. 6) does not self-aggregate and therefore they chose to demonstrate the results of hrPrP/RQ11+12 (SEQ ID No. 6) complex formation by electron microscopy (FIG. 18). Rather than using the acidic conditions of Nandi, they chose a buffer with a physiological pH (50 mM MOPS pH 7.5, 0.1 μg/μL tRNA, 8 μg/μL bovine calf serum, 0.05% NP40/deoxycholic acid). After a 16 hour incubation at room temperature, 8.9 pmoles of hrPrP did not form a discernible superstructure (FIG. 18a). However, if 0.16 pmoles of RQ11+12 (SEQ ID No. 6) were present in the reaction, an aggregated structure is can be observed (FIG. 18b). Although the superstructure formed between hrPrP appears to form a lattice-like aggregate, as opposed to SAFs recovered from scrapie-infected tissue that form discrete rod-like structures (Mere et al., 1981), the effect of RQ11+12 (SEQ ID No. 6) on hrPrP aggregation is clear and apparent.

This study confirms and extends the previously reported observations that ribonucleic acids bind to recombinant PrP. The results presented here demonstrate that hrPrP can form very stable complexes with several different RNAs with dissociation constants in the low nanomolar range. Two RNAs, RQ11+12 (SEQ ID No. 6) and MNV:AP1 (SEQ ID No. 3), bound to hrPrP very tightly and showed a resistance to competition from other RNAs and thereby showed a marked difference in binding activity as compared to some of the other RNAs in their test group. In addition, RQ11+12 (SEQ ID No. 6) presumably bound specifically to endogenous $PrP^C$ in whole mouse brain extracts. Although there are few apparent similarities between MNV:AP1 (SEQ ID No. 3) and RQ11+12 (SEQ ID No. 6) that would explain their specific binding to hrPrP, both are predicted to have secondary structural elements that contain thermodynamically stable non-canonical base pairs, a feature common to protein-binding RNAs. Non-Watson-Crick base pairs can widen the RNA deep groove, thereby accommodating interactions with extended protein domains and exposing additional hydrogen bonding groups that may play a role in protein ligand-binding specificity (Ye et al., 1999 Nat Struct Biol. 3(12):1026-33; Jiang et al., 1999 Structure Fold Des. 7(12):1461-72; Hermann and Westhof, 1999 Chem Biol 6(12):R335-43; Patel, 1999 Curr Opin Struct Biol 9(1):74-87; Puglisi and Williamson, 1999 in the RNA World, R F Gesteland, T R Cech, J F Atkins, eds., Cold Spring Harbor Laboratory Press, Cold Spring Harbor, N.Y., 2nd, 1999, pp 403-25; Hermann and Patel, 2000 Science 287(5454):820-5; the teachings of which are incorporated herein by reference). The previously described AP1 structure in MNV:AP1 (SEQ ID No. 3) has three stacked G-quartets (Weiss. et al. 1997), while RQ11+12 (SEQ ID No. 6) contains two RNA domains known to contain non-Watson-Crick base pairs—the Rev Binding Element (RBE) and the Sarcin/Ricin cleavage domain from 18S rRNA (FIG. 12d) (Iwai et al., 1992; Endo and Wool, 1982 J Biol Chem 257(15):9054-60; the teachings of which are incorporated herein by reference). The thermodynamic stability imparted by these RNA secondary structures may make possible a more extensive interaction with the flexible N-terminus of hrPrP. The unstructured peptide may alter its conformation to the architecture of the stable RNAs, thus forming a stable complex, as is the case in the binding between peptides derived from the HIV-1 Rev protein and its RNA aptamers (Ye I et al., 1996; Ye et al., 1999 Chem Biol 6(9):657-69; Tan et al., 1993 Cell 73(5): 1031-40; the teachings of which are incorporated herein by reference).

Figure 16:
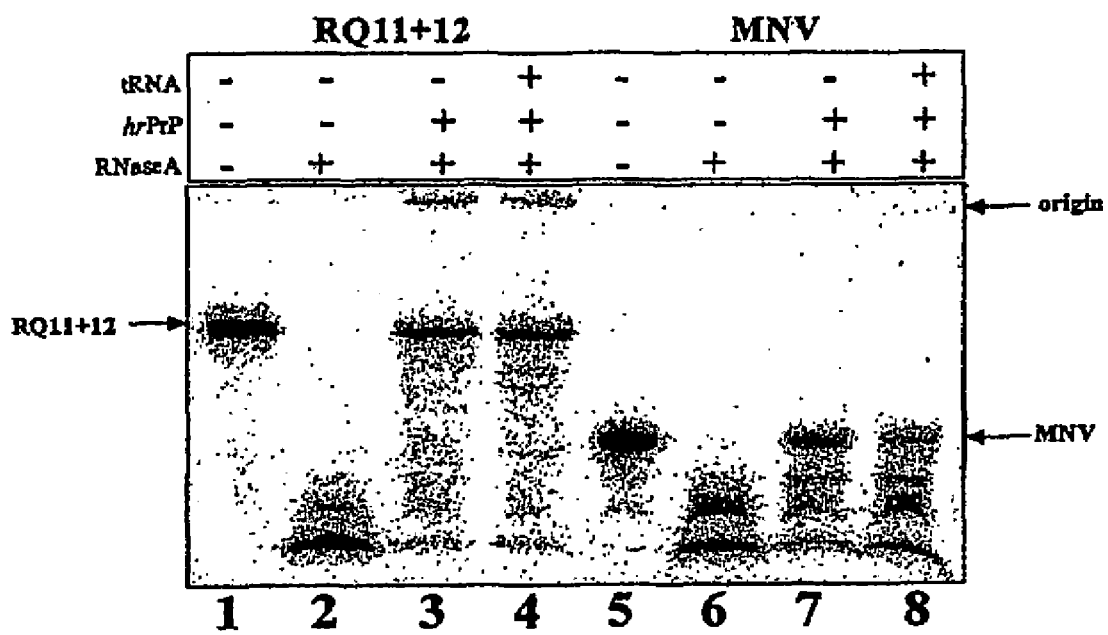
FIG. 16 shows results from an RnaseA protection study.

It was proposed that DNA can lower the energy of activation in the conversion of $PrP^C$ into $PrP^{Sc}$ by stabilizing a PrP intermediate through the formation of a DNA/protein complex. In this study, the inventors present data that may suggest a similar role for RNAs like RQ11+12 (SEQ ID No. 6). They demonstrate that RQ11+12 (SEQ ID No. 6) binding to PrP occurs at very low concentrations with high affinity and specificity in the presence of a vast molar excess of competitor RNA. The binding of hrPrP also protected RQ11+12 (SEQ ID No. 6) from degradation by RNaseA. These results present a model that a specific RNA interaction, typified by the interaction of RQ11+12 (SEQ ID No. 6) with hrPrP, could initiate the formation of RNA/PrP complexes, and even catalyze the formation of PrP aggregates. Such aggregates are predicted to be fibrillar and insoluble. Formation of such an aggregate may explain the amount of sample accumulated at the origin in the denaturing gel in FIG. 16, lanes 3 and 4. This may also explain the results of the self-competition binding experiments where RQ11+12 (SEQ ID No. 6) competes for its own binding to hrPrP more efficiently than MNV (SEQ ID No. 2) competes for its own binding (FIG. 16b). The effect becomes most apparent when the ratio of PrP to RNA approaches 1:1, which would be expected if RQ11+12 (SEQ ID No. 6) was binding to more than one molecule of hrPrP. Previously, the in vitro formation of PrP aggregates catalyzed by nucleic acids has been demonstrated with DNA under acidic conditions (Nandi and Leclerc, 1999; Nandi and Sizaret'2001; Cordeiro et. al., 2001 J Biol Chem 276(52):49400-09; the teachings of which are incorporated herein by reference). It is tempting to suggest that RQ11+12 (SEQ ID No. 6) catalyzes the formation of RNA/PrP aggregates. The effect is kinetic—RNAs like RQ11+12 (SEQ ID No. 6) can interact with PrP in a very particular way that can efficiently catalyze structural transformation. Due to the specificity of the interaction, it can occur at low concentrations. This activity may be related to the difference in binding activity between RNAs like RQ11+12 (SEQ ID No. 6) and RNAs like MNV (SEQ ID No. 2).

Due to the complexities of prion disease transmission, some recent studies have focused on the possibility that a cofactor may exist that assists in the initiation or progression of prion disease (Weissmann, 1991 Nature 352:679-83, the teachings of which are incorporated herein by reference). The search for a "factor X" protein that catalyzes the transformation from $PrP^C$ to $PrP^{Sc}$, the hallmark of prion diseases, has uncovered several possible protein candidates (Yehiely et al., 1997). Recently, it has been demonstrated that DNA can bind to PrP in vitro and induce fibrillation under special conditions (Nandi, 1998; Nandi and Leclerc, 1999; Nandi and Sizaret, 2001; Cordeiro et. al., 2001). This observation led one group to propose that DNA might play a role in the progression of prion diseases. The present data suggests that RNAs like RQ11+12 (SEQ ID No. 6) may be a more likely candidate for involvement prion disease. The $K_d$ of RQ11+12 (SEQ ID No. 6) for hrPrP is three orders of magnitude less than that measured for dsDNA, binding occurs under physiological conditions and the RNA would have the opportunity to interact with Prime, whose N-terminal domain extends into the endoplasmic reticulum (Hedge et al., 1998 Science 279(5352):827-34; the teachings of which are incorporated herein by reference). A model for the induction of PrP aggregation can be built around the structural change that the N-terminus of PrP undergoes upon the binding of a specific RNA ligand. The new conformation of the N-terminus may activate the fibrillation activity of the conserved amyloidogenic c region of PrP (amino acids 106 to 126) by exposing it to the solvent. A similar mechanism is followed in the fibrillation of the 90 Lisa amyloid precursor protein (APP) which aggregates only after the internal 42 amino acid, 6-amyloid peptide is excised from APP and becomes solvent exposed (Rochet and Lansbury, 2000 Curr Opin Struct Biol 10:60-8; the teachings of which are incorporated herein by reference). If this model were correct, the present results would suggest that an RNA molecule might be capable of inducing or accelerating fibril formation in prion diseases.

Regardless of the mechanism of binding to PrP or the role of specific RNAs in prion diseases, the inventors demonstrate that the RNA RQ11+12 (SEQ ID No. 6) is a capable probe for the PrP protein. In addition, RQ11+12 (SEQ ID No. 6) is a potent template for the RNA-dependent RNA polymerase, Q-beta replicase. This new type of bifunctional RNA molecule or amplibody has the ability to specifically bind to a protein target and to be amplified directly by Q-beta replicase. Molecules like RQ11+12 (SEQ ID No. 6) are useful not only in the study of prion biology, but also in the potential development of newer, more sensitive diagnostic technologies.

To facilitate the understanding of the present invention, a number of terms and phrases are defined below:

As used herein, the terms "polynucleotide" and "oligonucleotide" are used interchangeably, and include polymeric forms of nucleotides of any length, either deoxyribonucleotides or ribonucleotides, or analogs thereof. Polynucleotides can have any three-dimensional structure, and can perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be inputted into databases in a computer having a central processing unit and used for bioinformatics applications such as functional genomics and homology searching.

A "gene" includes a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art, some of which are described herein.

A "gene product" includes an amino acid, e.g., peptide or polypeptide, generated when a gene is transcribed and then translated.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, typically a thermally-stable polymerase enzyme. Methods for PCR are well known in the art, and are taught, for example, in MacPherson et al., IRL Press at Oxford University Press (1991). All processes of producing replicate copies of a polynucleotide, such as PCR or gene cloning, are collectively referred to herein as "replication". A primer can also be used as a probe in hybridization reactions, such as Southern or Northern blot analyses (see, for example, Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

The term "cDNAs" includes complementary DNA, that is mRNA molecules present in a cell or organism made into cDNA with an enzyme such as reverse transcriptase. A "cDNA library" includes a collection of mRNA molecules present in a cell or organism, converted into cDNA molecules with the enzyme reverse transcriptase, then inserted into "vectors" (other DNA molecules that can continue to replicate after addition of foreign DNA). Exemplary vectors for libraries include bacteriophage, viruses that infect bacteria, e.g., λ phage. The library can then be probed for the specific cDNA (and thus mRNA) of interest.

A "delivery vehicle" includes a molecule that is capable of inserting one or more polynucleotides into a host cell. Examples of delivery vehicles are liposomes, biocompatible polymers, including natural polymers and synthetic polymers; lipoproteins; polypeptides; polysaccharides; lipopolysaccharides; artificial viral envelopes; metal particles; and bacteria, viruses and viral vectors, such as baculovirus, adenovirus, and retrovirus, bacteriophage, cosmid, plasmid, fungal vector and other recombination vehicles typically used in the art which have been described for replication and/or expression in a variety of eukaryotic and prokaryotic hosts. The delivery vehicles may be used for replication of the inserted polynucleotide, gene therapy as well as for simply polypeptide and protein expression.

A "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

A "host cell" is intended to include any individual cell or cell culture that can be or has been a recipient for vectors or for the incorporation of exogenous nucleic acid molecules, polynucleotides and/or proteins. It also is intended to include progeny of a single cell. The progeny may not necessarily be completely identical (in morphology or in genomic or total DNA complement) to the original parent cell due to natural, accidental, or deliberate mutation. The cells may be prokaryotic, include but are not limited to bacterial cells.

The term "genetically modified" includes a cell containing and/or expressing a foreign gene or nucleic acid sequence that in turn modifies the genotype or phenotype of the cell or its progeny. This term includes any addition, deletion, or disruption to a cell's endogenous nucleotides.

As used herein, "expression" includes the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

"Differentially expressed", as applied to a gene, includes the differential production of mRNA transcribed from a gene or a protein product encoded by the gene. A differentially expressed gene may be overexpressed or underexpressed as compared to the expression level of a normal or control cell. In one aspect, it includes a differential that is 2.5 times, preferably 5 times or preferably 10 times higher or lower than the expression level detected in a control sample. The term "differentially expressed" also includes nucleotide sequences in a cell or tissue which are expressed where silent in a control cell or not expressed where expressed in a control cell.

The term "polypeptide" includes a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

"Hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency." The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C.

When hybridization occurs in an antiparallel configuration between two single-stranded polynucleotides, the reaction is called "annealing" and those polynucleotides are described as "conplementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

As used herein, the term "nucleic acid molecule" is intended to include DNA molecules, e.g., cDNA or genomic DNA, and RNA molecules, e.g., mRNA, and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules, which are separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated marker nucleic acid molecule of the invention, or nucleic acid molecule encoding a polypeptide marker of the invention, can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO. 1-10, or a portion thereof, can be isolated using standard molecular biology techniques and the sequence information provided herein. Using all or portion of the nucleic acid sequence of SEQ ID NO. 1-10 as a hybridization probe, a molecule comprising SEQ ID NO. 1-10 can be isolated using standard hybridization and cloning techniques as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to marker nucleotide sequences, or nucleotide sequences encoding a marker of the invention can be prepared by standard synthetic techniques, e.g., using an automated DNA synthesizer.

In another embodiment, an isolated nucleic acid molecule of the invention comprises a nucleic acid molecule which is a complement of the nucleotide sequence of SEQ ID NO. 1-10, or a portion thereof. A nucleic acid molecule that is complementary to such a nucleotide sequence is one which is sufficiently complementary to the nucleotide sequence such that it can hybridize to the nucleotide sequence, thereby forming a stable duplex.

The nucleic acid molecule of the invention, moreover, can comprise only a portion of the nucleic acid sequence of SEQ ID NO 1-10 of the invention, or a fragment which can be used as a probe or primer. The probe/primer typically comprises substantially purified oligonucleotide.

Probes based on the nucleotide sequence of a nucleic acid molecule encoding SEQ ID NO 1-10 can be used to detect agglomeration proteins. In other embodiments, the probe comprises a labeling group attached thereto, e.g., the labeling group can be a radioisotope, a fluorescent compound, an enzyme, or an enzyme co-factor. Such probes can be used as a part of a diagnostic test kit for identifying cells or tissue which misexpresses, e.g., over- or under-express, a polypeptide of the invention, or which have greater or fewer copies of a gene of the invention.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO. 1-10. As used herein, a "naturally-occurring" nucleic acid molecule includes an RNA or DNA molecule having a nucleotide sequence that occurs in nature, e.g., encodes a natural protein.

In other embodiments, the oligonucleotides of the invention can include other appended groups such as peptides, e.g., for targeting host cell receptors in vivo, or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. W088/09810) or the blood-brain barrier (see, e.g., PCT Publication No. WO 89/10134). In addition, oligonucleotides can be modified with hybridization-triggered cleavage agents (see, Krol et al. (1988) *Bio-Techniques* 6:958-976) or intercalating agents (see, Zon (1988) *Pharm. Res.* 5:539-549). To this end, the oligonucleotide may be conjugated to another molecule, e.g., a peptide, hybridization triggered cross-linking agent, transport agent, or hybridization-triggered cleavage agent. Finally, the oligonucleotide may be detectably labeled, either such that the label is detected by the addition of another reagent, e.g., a substrate for an enzymatic label, or is detectable immediately upon hybridization of the nucleotide, e.g., a radioactive label or a fluorescent label, e.g., a molecular beacon as described in U.S. Pat. No. 5,876,930.

Another aspect of the invention pertains to vectors, preferably expression vectors, containing a nucleic acid encoding a marker protein of the invention (or a portion thereof). As used herein, the term "vector" includes a nucleic acid molecule capable of transporting another nucleic acid to which it has been linked. One type of vector is a "plasmid", which includes a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced, e.g., bacterial vectors having a bacterial origin of replication and episomal mammalian vectors. Other vectors, e.g., non-episomal mammalian vectors, are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence, e.g., in an in vitro transcription/translation system or in a host cell when the vector is introduced into the host cell. The term "regulatory sequence" is intended to include promoters, enhancers and other expression control elements, e.g., polyadenylation signals. Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells, e.g., tissue-specific regulatory sequences. It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein, e.g., marker proteins, mutant forms of marker proteins, fusion proteins, and the like.

The recombinant expression vectors of the invention can be designed for expression of marker proteins in prokaryotic or eukaryotic cells. For example, proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in marker activity assays, e.g., direct assays or competitive assays described in detail below, or to generate antibodies specific for marker proteins for example.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

Another aspect of the invention pertains to host cells into which a nucleic acid molecule of the invention is introduced within a recombinant expression vector or a nucleic acid molecule of the invention containing sequences which allow it to homologously recombine into a specific site of the host cell's genome. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. Preferably, the host cell is a prokaryotic cell. For example, the invention can be expressed in bacterial cells such as *E. coli*. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid, e.g., DNA, into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989), and other laboratory manuals.

A host cell of the invention, such as a host cell in culture, can be used to produce, i.e., express, a recombinant protein. Accordingly, the invention further provides methods for producing a protein using the host cells of the invention. In one embodiment, the method comprises culturing the host cell of invention (into which a recombinant expression vector encoding a protein, or proteins, has been introduced) in a suitable medium such that a protein of the invention is produced. In another embodiment, the method farther comprises isolating a protein from the medium or the host cell.

Of course, one skilled in the art will appreciate further features and advantages of the invention based on the above-described embodiments. Accordingly, the invention is not to be limited by what has been particularly shown and described, except as indicated by the appended claims.

What is claimed is:
1. An isolated RNA molecule or derivative thereof, comprising the sequence according to SEQ ID NO:6.

* * * * *